(12) United States Patent
Goral

(10) Patent No.: US 8,463,626 B1
(45) Date of Patent: Jun. 11, 2013

(54) SYSTEMS AND METHODS OF AUTOMATING RECONSIDERATION OF CARDIAC RISK

(75) Inventor: James E. Goral, San Antonio, TX (US)

(73) Assignee: United Services Automobile Association (USAA), San Antonio, TX (US)

( * ) Notice: Subject to any disclaimer, the term of this patent is extended or adjusted under 35 U.S.C. 154(b) by 252 days.

(21) Appl. No.: 13/079,873

(22) Filed: Apr. 5, 2011

Related U.S. Application Data

(63) Continuation of application No. 11/829,777, filed on Jul. 27, 2007, now Pat. No. 7,945,462, which is a continuation-in-part of application No. 11/320,553, filed on Dec. 28, 2005, and a continuation-in-part of application No. 11/320,540, filed on Dec. 28, 2005, and a continuation-in-part of application No. 11/320,172, filed on Dec. 28, 2005, now abandoned.

(60) Provisional application No. 60/915,667, filed on May 2, 2007.

(51) Int. Cl.
*G06Q 10/00* (2012.01)
*G06Q 50/00* (2012.01)
*G06Q 40/00* (2012.01)

(52) U.S. Cl.
USPC .................................. 705/4; 705/2; 705/3

(58) Field of Classification Search
USPC ........................................................ 705/2–4
See application file for complete search history.

(56) References Cited

U.S. PATENT DOCUMENTS

| | | | | |
|---|---|---|---|---|
| 4,975,840 | A * | 12/1990 | DeTore et al. | 705/4 |
| 2003/0195776 | A1 * | 10/2003 | Moore et al. | 705/4 |
| 2005/0131742 | A1 * | 6/2005 | Hoffman et al. | 705/4 |
| 2008/0004915 | A1 * | 1/2008 | Brown | 705/4 |

\* cited by examiner

*Primary Examiner* — Neal Sereboff
(74) *Attorney, Agent, or Firm* — Kilpatrick Townsend & Stockton LLP

(57) ABSTRACT

Systems, methods, and computer-readable media to automate reconsideration of a cardiac risk category associated with issuance of a life insurance policy may provide an indication of a best potential risk category or rate class that would be available if at least one action is completed by a life insurance applicant.

21 Claims, 19 Drawing Sheets

ECG Reconsideration Risk Calculator 401

| | | 402 | 403 | 404 | 405 |
|---|---|---|---|---|---|
| 1 | Mechanical (Artificial) Pacemaker | Mechanical (Artificial) Pacemaker: ▼ | MIB Codes 900#X#(1) | Needed for Reconsideration<br>ECHO, ETT AND AGE < 40<br>ECHO, ETT AND AGE 40-59<br>ECHO, ETT AND AGE > 59 | Best Potential Rate Class<br>TABLE B<br>PREF<br>PREF |
| 2 | Dysrhythmias | Dysrhythmias: ▼ | MIB Codes 900#X#(2) | Needed for Reconsideration<br>ECHO, ETT | Best Potential Rate Class<br>PUL |
| 3 | Premature Contractions | PVCs < 3 on ECG ▼ | MIB Codes 900#X# | Needed for Reconsideration<br>NONE | Best Potential Rate Class<br>PUL |
| 4 | Rate | Sinus Bradycardia, > 40/min but < 45/min ▼ | MIB Codes 900#X#(4B) | Needed for Reconsideration<br>NONE | Best Potential Rate Class<br>PUL |
| 5 | Atrial Fibrillation and/or Flutter | Atrial Fibrillation and/or Flutter New ▼ | MIB Codes 900#X#(7) | Needed for Reconsideration<br>MD EVALUATION, ECHO, ETT | Best Potential Rate Class<br>TABLE D |
| 6 | AV (Atrio-Ventricular) Block | First Degree AV Block (PR>0.28 sec) ▼ | MIB Codes 900#X#(8A) | Needed for Reconsideration<br>OLD ECG > 2 YRS SHOWING SAME<br>ECHO<br>ETT<br>ECHO AND ETT | Best Potential Rate Class<br>PREF<br>1 TABLE REDUCED<br>1 TABLE REDUCED<br>PREF |
| 7 | Wolf-Parkinson-White Syndrome (WPW) | WPW Ablated > 6 mo. ▼ | MIB Codes 900#X#(9) | Needed for Reconsideration<br>NO RECURRENCES<br>PALPITATIONS | Best Potential Rate Class<br>PUL |
| 8 | Q-Waves, Abnormal | R>S-Wave in V1, no RAD or Heart Disease ▼ | MIB Codes 900#X#(12E) | Needed for Reconsideration<br>NONE | Best Potential Rate Class<br>PUL |

FIG. 10A

| ECG_INTERPRETATION | MIB | NEEDED FOR RECONSIDERATION | BEST POTENTIAL RATE CLASS |
|---|---|---|---|
| Mechanical (Artificial) Pacemaker: | 900#X#(1) | ECHO, ETT AND AGE <40 | TABLE B |
| | | ECHO, ETT AND AGE 40-59 | PREF |
| | | ECHO, ETT AND AGE >59 | PREF |
| Dysrhythmias: | 900#X#(2) | ECHO, ETT | PUL |
| Premature Contractions: | | | |
| PVCs < 3 on ECG | 900#X# | NONE | PUL |
| PACs 3-8 on ECG | 900#X#(3A) | NONE | PUL |
| PVCs 3-20 on ECG | 900#X#(3C) | ECHO | 1 TABLE REDUCED |
| | | ETT | 1 TABLE REDUCED |
| | | ECHO AND ETT | PUL |
| Complex PVCs (Bigeminy, Trigeminy, Couplets, Triplets or > 20 PVD on ECG) | 900#X#(3D) | ECHO | 1 TABLE REDUCED |
| | | ETT | 1 TABLE REDUCED |
| | | ECHO AND ETT | PREF |
| PACs > 8 on ECG | 900#X#(3A) | ECHO | 1 TABLE REDUCED |
| | | ETT | 1 TABLE REDUCED |
| | | HOLTER | 1 TABLE REDUCED |
| | | ECHO, ETT AND HOLTER | PUL |
| Rate: | | | |
| Sinus Tachycardia, Exceeding 110/min. | 900#X#(4A) | MD EVALUATION | PUL |
| | | HOLTER | PREF |
| | | ECHO AND ETT | PUL |
| Sinus Bradycardia, Greater Than 40/min. But < 45/min. | 900#X#(4B) | NONE | PUL |
| Sinus Bradycardia, Less Than 40/ min. | 900#X#(4B) | ECHO | PREF |
| | | ETT | PREF |
| | | HOLTER | PREF |
| | | ECHO AND ETT | PUL |
| Atrial Fibrillation And/Or Flutter: | | | |
| Atrial Fibrillation and/or Flutter New | 900#X#(7) | MD EVALUATION, ECHO, ETT | TABLE D |

FIG. 11A

| ECG_INTERPRETATION, cont. | MIB | NEEDED FOR RECONSIDERATION | BEST POTENTIAL RATE CLASS |
|---|---|---|---|
| Atrial Fibrillation and/or Flutter Old | 900#X#(7) | OLD ECG >5YRS SHOWING SAME | PREF |
| | | ECHO | 1 TABLE REDUCED |
| | | ETT | 1 TABLE REDUCED |
| | | ECHO, ETT | PREF |
| AV (Atrio-Ventricular) Block: | | | |
| First Degree AV Block (PR < 0.28 sec.) | 900#X#(8A) | NONE | PUL |
| First Degree AV Block (PR > 0.28 sec.) | 900#X#(8A) | OLD ECG >2YRS SHOWING SAME | PREF |
| | | ECHO | 1 TABLE REDUCED |
| | | ETT | 1 TABLE REDUCED |
| | | ECHO AND ETT | PREF |
| Second Degree AV Block, Mobitz I, Wenckebach | 900#X#(8B) | NONE | PREF |
| Second Degree AV Block, Mobitz II, Non-Wenckebach | 900#X#(8C) | ECHO, ETT, HOLTER | TABLE B |
| Third Degree AV Block or Complete AV Dissociation | 900#X#(8D) | PACEMAKER AGE <40 | TABLE B |
| | | PACEMAKER AGE 40-59 | PREF |
| | | PACEMAKER AGE >59 | PREF |
| Wolf-Parkinson-White Syndrome (WPW): | | | |
| Wolf-Parkinson-White Syndrome (WPW) Ablated > 6 mo. | 900#X#(9) | NO RECURRANCES PALPITATIONS | PUL |
| Wolf-Parkinson-White Syndrome (WPW), No Arrhythmia | 900#X#(9) | NO RECURRANCES PALPITATIONS | PUL |
| Q-Waves, Abnormal: | | | |
| Lead 2 and/or 3 and AVF | 900#X#(12A) | ECHO | PREF |
| | | ETT | PREF |
| | | ECHO AND ETT | PUL |
| | | CARDIAC CATHETERIZATION | PUL |
| Lead 1, AVL, and V6 | 900#X#(12B) | ECHO | PREF |
| | | ETT | PREF |

FIG. 11B

| ECG_INTERPRETATION, cont. | MIB | NEEDED FOR RECONSIDERATION | BEST POTENTIAL RATE CLASS |
|---|---|---|---|
| | | ECHO AND ETT | PUL |
| | | CARDIAC CATHETERIZATION | PUL |
| Leads V2, Only | 900#X#(12C) | REPEAT ECG | PUL |
| | | ECHO | PUL |
| | | ETT | PUL |
| | | ECHO AND ETT | PUL |
| | | CARDIAC CATHETERIZATION | PUL |
| Leads V2 Through V6, Two or More | 900#X#(12C) | REPEAT ECG | PUL |
| | | ECHO | PREF |
| | | ETT | PREF |
| | | ECHO AND ETT | PUL |
| | | CARDIAC CATHETERIZATION | PUL |
| Poor R-Wave Progression--Males Age < 40 | 900#X#(12D) | REPEAT ECG | PUL |
| | | ECHO | PUL |
| | | ETT | PREF |
| | | ECHO AND ETT | PUL |
| | | CATHETERIZATION | PUL |
| Poor R-Wave Progression--Males Age > 40 | 900#X#(12D) | REPEAT ECG | PUL |
| | | ECHO | PUL |
| | | ETT | PREF |
| | | ECHO AND ETT | PUL |
| | | CATHETERIZATION | PUL |
| Poor R-Wave Progression--Females | 900#X#(12D) | REPEAT ECG | PUL |
| | | ECHO | PUL |
| | | ETT | PUL |
| | | CATHETERIZATION | PUL |
| R>S-Wave in V1, no RAD or Heart Disease | 900#X#(12E) | NONE | PUL |
| R>S Wave in V1 Suspicious of Heart of Lung Disease | 900#X#(12E) | ECHO | PUL |
| Voltage Abnormal: | | | |
| Left Ventricular Hypertrophy, No Hypertension | 900#X#(13A) | ECHO | PUL |

FIG. 11C

| ECG_INTERPRETATION, cont. | MIB | NEEDED FOR RECONSIDERATION | BEST POTENTIAL RATE CLASS |
|---|---|---|---|
| Left Ventricular Hypertrophy With Hypertension | 900#X#(13A) | ECHO | PUL |
| Low Voltage, No COPD or Hypothyroid | 900#X#(13B) | ECHO | PUL |
|  |  | THYROID STUDIES | PREF |
| Axis Deviation, Abnormal: |  |  |  |
| Right Axis Deviation, No Heart or Lung Disease | 900#X#(14A) | NONE | PUL |
| Right Axis Deviation With Heart or Lung Disease | 900#X#(14A) | ECHO | PUL |
| Left Axis Deviation, Axis > -45 and/or LAFB | 900#X#(14B) | ECHO | 1 TABLE REDUCED |
|  |  | ETT | PUL |
| ST Segment Depression and/or T-Waves, Abnormal: |  |  |  |
| ST Segment Depression < 1 mm | 900#X#(16A) | ECHO | PREF |
|  |  | ETT | PUL |
|  |  | CATHETERIZATION | PUL |
| ST Segment Depression > 1 mm | 900#X#(16A) | ECHO | PREF |
|  |  | ETT | PUL |
|  |  | CATHETERIZATION | PUL |
| T-Wave Inversions (Minor Changes) < 1 mm | 900#X#(16B) | ECHO | PREF |
|  |  | ETT | PREF |
|  |  | ECHO AND ETT | PUL |
|  |  | CATHETERIZATION | PUL |
| T-Wave Inversions (Major Changes) > 1 mm | 900#X#(16B) | ECHO | 2 TABLE REDUCED |
|  |  | ETT | 2 TABLE REDUCED |
|  |  | ECHO AND ETT | PUL |
|  |  | CATHETERIZATION | PUL |

FIG. 11D

| ECG_INTERPRETATION, cont. | MIB | NEEDED FOR RECONSIDERATION | BEST POTENTIAL RATE CLASS |
|---|---|---|---|
| Low, Flat or Minor Diphasic T-Wave (Minor Changes) | 900#X#(16C) | ECHO | PREF |
| | | ETT | PUL |
| | | | |
| ST Segment, Abnormal Elevation > 1mm | 900#X#(16D) | ECHO | PREF |
| | | ETT | PREF |
| | | ECHO AND ETT | PUL |
| | | | |
| Bundle Branch Block: | | | |
| Right Bundle Branch Block, Complete, Age < 40 | 900#X#(17A) | ETT | PUL |
| Right Bundle Branch Block, Complete, Age > 40 | 900#X#(17A) | OLD ECG OVER 5 YRS | PREF |
| | | ETT | 1 TABLE REDUCED |
| | | | |
| Right Bundle Branch Block, Complete | 900#X#(17A-14B) | OLD ECG OVER 5 YRS AGE > OR = 40 | PREF |
| | | OLD ECG OVER 5 YRS AGE < 40 | PUL |
| and Left Anterior Fasicular Block | | ETT | 1 TABLE REDUCED |
| | | | |
| Left Bundle Branch Block, Complete, New <1 yr. | 900#X#(17B) | ECHO | 1 TABLE REDUCED |
| | | ECHO-ETT OR CARDIOLYTE-ETT | 1 TABLE REDUCED |
| | | ECHO AND ECHO/CARDIOLYTE-ETT | 2 TABLE REDUCED |
| | | CATHETERIZATION | PREF |
| | | | |
| Left Bundle Branch Block, Complete, 1-5 years | 900#X#(17B) | OLD ECG OVER 5 YRS | PREF |
| | | ECHO | 1 TABLE REDUCED |
| | | ECHOETT OR CARDIOLYTE ETT | 1 TABLE REDUCED |
| | | ECHO AND ECHO/CARDIOLYTE-ETT | 2 TABLE REDUCED |
| | | CATHETERIZATION | PREF |
| | | | |
| Left Bundle Branch Block, Complete, >5 yrs. | 900#X#(17B) | ECHO | 1 TABLE REDUCED |
| | | ECHOETT OR CARDIOLYTE ETT | PREF |
| | | | |
| Indeterminate Bundle Branch Block (QRS >0.12 sec.) | 900#X#(17C) | ECHO | 1 TABLE REDUCED |
| | | ETT | 1 TABLE REDUCED |

FIG. 11E

| ECG_INTERPRETATION, cont. | MIB | NEEDED FOR RECONSIDERATION | BEST POTENTIAL RATE CLASS |
|---|---|---|---|
| | | ECHO AND ETT | PREF |
| | | CATHETERIZATION | PREF |
| Incomplete Right Bundle Branch Block (QRS < 0.12 sec.) | 900#X#(17D) | NONE | PUL |
| Complex Cardiac Tests | | | |
| ETT | 900 (24B) | Nuclear Imaged Heart-Cardiolyte Ett | PUL |
| | | or EchoETT | |
| Nuclear Imaged Scan - Cardiolyte ETT or Thallium ETT | 935J | Catheterization | PUL |
| Echo ETT | 933J | Catheterization | PUL |
| Echo | 931J | Repeat Echo | Reconsideration |
| Holter | 900 (6B) | Repeat Holter | Refer to Med. Director |
| | | ETT | 1 Table Reduced |
| | | Echo | 1 Table Reduced |
| EBCT | 939J | ETT | PREF |
| | | Nuclear Imaged Heart-Cardiolyte Ett | PREF |

FIG. 11F

SYSTEMS AND METHODS OF AUTOMATING RECONSIDERATION OF CARDIAC RISK

RELATED APPLICATIONS

This application is a continuation of, and claims priority under 35 U.S.C. §120 for U.S. patent application Ser. No. 11/829,777, filed Jul. 27, 2007, entitled "Systems and Methods of Automating Reconsideration of Cardiac Risk", which in turn claims the benefit of:

U.S. Provisional Application No. 60/915,667, filed May 2, 2007, and is also a continuation-in-part of the following U.S. patent applications:

U.S. patent application Ser. No. 11/320,540, filed Dec. 28, 2005, entitled "Medical Diagnosis Interpretation Calculator";

U.S. patent application Ser. No. 11/320,172, filed Dec. 28, 2005, entitled "Medical Diagnosis Interpretation Calculator"; and U.S. patent application Ser. No. 11/320,553, filed Dec. 28, 2005, entitled "Medical Diagnosis Interpretation Calculator".

COPYRIGHT NOTICE AND PERMISSION

A portion of the disclosure of this patent document may contain material that is subject to copyright protection. The copyright owner has no objection to the facsimile reproduction by anyone of the patent document or the patent disclosure, as it appears in the U.S. Patent and Trademark Office patent files or records, but otherwise reserves all copyright rights whatsoever. The following notice shall apply to this document: Copyright © 2007, USAA.

BACKGROUND

Currently, electrocardiograms that are considered abnormal and associated with higher mortality are assigned a less than favorable risk classification. Life insurance (Life) underwriters and sales case analysts often are asked by applicants what additional information or tests could be provided to obtain an improved rating. Due to the highly technical aspect of these tests and associated mortality assumptions, these questions are often referred to the life insurance company's medical director (Medical Director). The term "Medical Director" as used herein means a physician or other person having relatively more medical expertise than an underwriter or sales case analyst. The Medical Director must then review the application file and advise the underwriter or sales case analyst on what additional information would improve the risk assessment of the abnormal electrocardiogram. This may delay processing time by several days and may increase demand on the Medical Director's time. If the medical director is not consulted on such applications and or the member applicant not properly advised, this may result in a customer paying either excessive rates or declining coverage, or in the company providing insurance to applicants with unreasonably high mortality risk, causing unnecessary financial loss.

Thus, systems and methods are needed that address the shortcomings of the prior art.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

In consideration of the above-identified shortcomings of the art, systems and methods for an interactive, self-service resource to reassess cardiac risk are provided. Various embodiments, including systems, methods, and computer-readable media, to automate reconsideration of a cardiac risk category associated with issuance of a life insurance policy may provide an indication of a best potential risk category or rate class that would be available if at least one action is completed by a life insurance applicant.

Below is a description of other advantages and features of the inventive subject matter.

BRIEF DESCRIPTION OF THE DRAWINGS

A life insurance underwriting risk calculator is further described with reference to the accompanying drawings in which:

FIGS. 10A and 10B together constitute a graphical user interface of an example electrocardiogram (ECG) reconsideration risk calculator portion of an example system comprising a life insurance underwriting risk calculator;

FIGS. 11A-11F together constitute an example table calculator as part of an embodiment of an electrocardiogram (ECG) reconsideration risk calculator 401;

DETAILED DESCRIPTION

Certain specific details are set forth in the following description and figures to provide a thorough understanding of various embodiments of the inventive subject matter. Certain well-known details often associated with computing and software technology are not set forth in the following disclosure to avoid unnecessarily obscuring the various embodiments of the inventive subject matter. Further, those of ordinary skill in the relevant art will understand that they can practice other embodiments of the inventive subject matter without one or more of the details described below. Finally, while various methods are described with reference to operations and sequences in the following disclosure, the description as such is for providing a clear implementation of embodiments of the inventive subject matter, and the operations and sequences of operations should not be taken as required to practice this inventive subject matter.

Example Computing Devices

Figure 1:
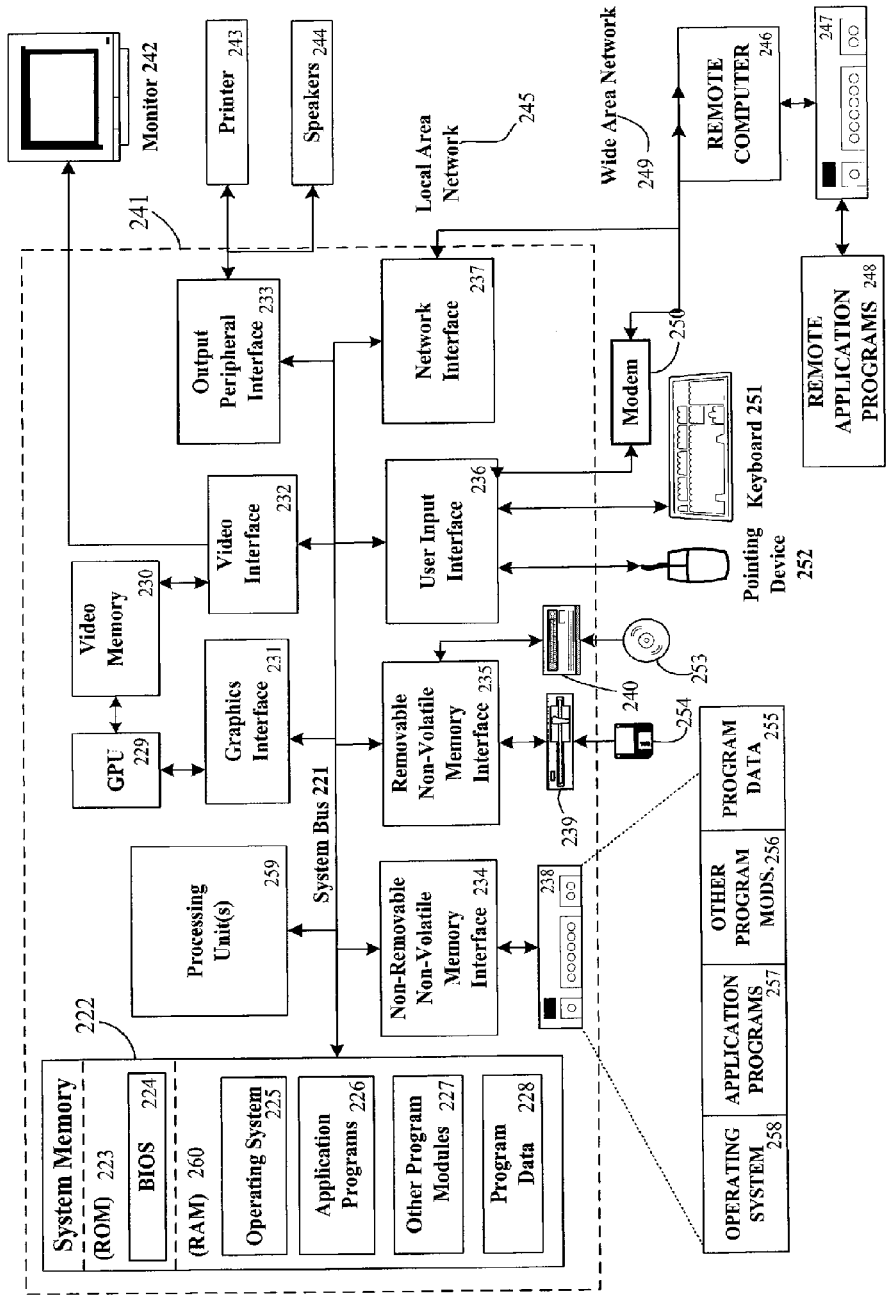
FIG. 1 is a block diagram representing an exemplary computing device suitable for use in conjunction with providing a life insurance underwriting risk calculator.

Referring to FIG. 1, shown is a block diagram representing an exemplary computing device suitable for use in conjunction with implementing the processes described above. For example, the computer-executable instructions that carry out the processes and methods for a life insurance underwriting risk calculator may reside and/or be executed in such a computing environment as shown in FIG. 1. The computing system environment 220 is only one example of a suitable computing environment and is not intended to suggest any limitation as to the scope of use or functionality of the inventive subject matter. Neither should the computing environment 220 be interpreted as having any dependency or requirement relating to any one or combination of components illustrated in the exemplary operating environment 220.

Aspects of the inventive subject matter are operational with numerous other general purpose or special purpose computing system environments or configurations. Examples of well known computing systems, environments, and/or configurations that may be suitable for use with the inventive subject matter include, but are not limited to, personal computers, server computers, hand-held or laptop devices, multiprocessor systems, microprocessor-based systems, set-top boxes, programmable consumer electronics, network PCs, minicomputers, mainframe computers, distributed computing environments that include any of the above systems or devices, and the like.

Aspects of the inventive subject matter may be implemented in the general context of computer-executable instructions, such as program modules, being executed by a computer. Generally, program modules include routines, programs, objects, components, data structures, etc. that perform particular tasks or implement particular abstract data types. Aspects of the inventive subject matter may also be practiced in distributed computing environments where tasks are performed by remote processing devices that are linked through a communications network. In a distributed computing environment, program modules may be located in both local and remote computer storage media including memory storage devices.

An exemplary system for implementing aspects of the inventive subject matter includes a general purpose computing device in the form of a computer 241. Components and/or subsystems or modules of computer 241 may include, but are not limited to, a processing unit 259, a system memory 222, and a system bus 221 that couples various system components including the system memory to the processing unit 259. The system bus 221 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, the Peripheral Component Interconnect (PCI) bus also known as Mezzanine bus, as well as its successor, the PCI-Express standard.

Computer 241 typically includes a variety of computer-readable media. Computer-readable media can be any available media that can be accessed by computer 241 and includes both volatile and nonvolatile media, removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules, or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage, or other magnetic storage devices, or any other medium that can be used to store the desired information and that can be accessed by computer 241. Communication media typically embodies computer-readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared, and other wireless media. Combinations of the any of the above should also be included within the scope of computer-readable media.

The system memory 222 includes computer storage media in the form of volatile and/or nonvolatile memory such as read only memory (ROM) 223 and random access memory (RAM) 260. A basic input/output system 224 (BIOS), containing the basic routines that help to transfer information between elements within computer 241, such as during start-up, is typically stored in ROM 223. RAM 260 typically contains data and/or program modules that are immediately accessible to and/or presently being operated on by processing unit 259. By way of example, and not limitation, FIG. 1 illustrates operating system 225, application programs 226, other program modules 227, and program data 228.

The computer 241 may also include other removable/non-removable, volatile/nonvolatile computer storage media. By way of example only, FIG. 1 illustrates a hard disk drive 238 that reads from or writes to non-removable, nonvolatile magnetic media, a magnetic disk drive 239 that reads from or writes to a removable, nonvolatile magnetic disk 254, and an optical disk drive 240 that reads from or writes to a removable, nonvolatile optical disk 253 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 238 is typically connected to the system bus 221 through a non-removable memory interface such as interface 234, and magnetic disk drive 239 and optical disk drive 240 are typically connected to the system bus 221 by a removable memory interface, such as interface 235.

The drives and their associated computer storage media discussed above and illustrated in FIG. 1, provide storage of computer-readable instructions, data structures, program modules, and other data for the computer 241. In FIG. 1, for example, hard disk drive 238 is illustrated as storing operating system 258, application programs 257, other program modules 256, and program data 255. Note that these components can either be the same as or different from operating system 225, application programs 226, other program modules 227, and program data 228. Operating system 258, application programs 257, other program modules 256, and program data 255 are given different numbers here to illustrate that, at a minimum, they are different copies. A user may enter commands and information into the computer 241 through input devices such as a keyboard 251 and pointing device 252, commonly referred to as a mouse, trackball, or touch pad.

Other input devices (not shown) may include a microphone, joystick, game pad, satellite dish, scanner, or the like. These and other input devices are often connected to the processing unit 259 through a user input interface 236 that is coupled to the system bus, but they may be connected by other interface and bus structures, such as a parallel port, game port, or a universal serial bus (USB). A monitor 242 or other type of display device is also connected to the system bus 221 via an interface, such as an insecure or secure video interface 232. An exemplary secure video standard would be the High-Definition Multimedia Interface (HDMI) standard. In addition to the monitor, computers may also include other peripheral output devices such as speakers 244 and printer 243, which may be connected through an output peripheral interface 233.

The computer 241 may operate in a networked environment using logical connections to one or more remote computers, such as a remote computer 246. The remote computer 246 may be a personal computer, a server, a router, a network PC, a peer device, or other common network node, and it typically includes many or all of the elements described above relative to the computer 241, although only a memory storage device 247 has been illustrated in FIG. 1. The logical connections depicted in FIG. 1 include a local area network (LAN) 245 and a wide area network (WAN) 249, but they may also include other networks. Such networking environments are commonplace in offices, enterprise-wide computer networks, intranets, and the Internet.

When used in a LAN networking environment, the computer 241 is connected to the LAN 245 through a network interface or adapter 237. When used in a WAN networking environment, the computer 241 typically includes a modem 250 or other means for establishing communications over the WAN 249, such as the Internet. The modem 250, which may be internal or external, may be connected to the system bus 221 via the user input interface 236, or other appropriate mechanism. In a networked environment, program modules depicted relative to the computer 241, or portions thereof, may be stored in the remote memory storage device. By way of example, and not limitation, FIG. 1 illustrates remote application programs 248 as residing on memory device 247. It will be appreciated that the network connections shown are exemplary and other means of establishing a communications link between the computers may be used.

It should be understood that the various techniques described herein may be implemented in connection with hardware or software or, where appropriate, with a combination of both. Thus, the methods and apparatus of the inventive subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computer, the machine becomes an apparatus for practicing the inventive subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the inventive subject matter, e.g., through the use of an API, reusable controls, or the like. Such programs are preferably implemented in a high level procedural or object oriented programming language to communicate with a computer system. However, the program(s) can be implemented in assembly or machine language, if desired. In any case, the language may be a compiled or interpreted language, and combined with hardware implementations.

Although exemplary embodiments may refer to utilizing aspects of the inventive subject matter in the context of one or more stand-alone computer systems, the inventive subject matter is not so limited, but rather it may be implemented in connection with any computing environment, such as a network or distributed computing environment. Still further, aspects of the inventive subject matter may be implemented in or across a plurality of processing chips or devices, and storage may similarly be effected across a plurality of devices. Such devices might include personal computers, network servers, handheld devices, supercomputers, or computers integrated into other systems such as automobiles and airplanes.

In light of the diverse computing environments that may be built according to the general framework provided in FIG. 1, the systems and methods provided herein cannot be construed as limited in any way to a particular computing architecture. Instead, the inventive subject matter should not be limited to any single embodiment, but rather it should be construed in breadth and scope in accordance with the appended claims.

Figure 2:
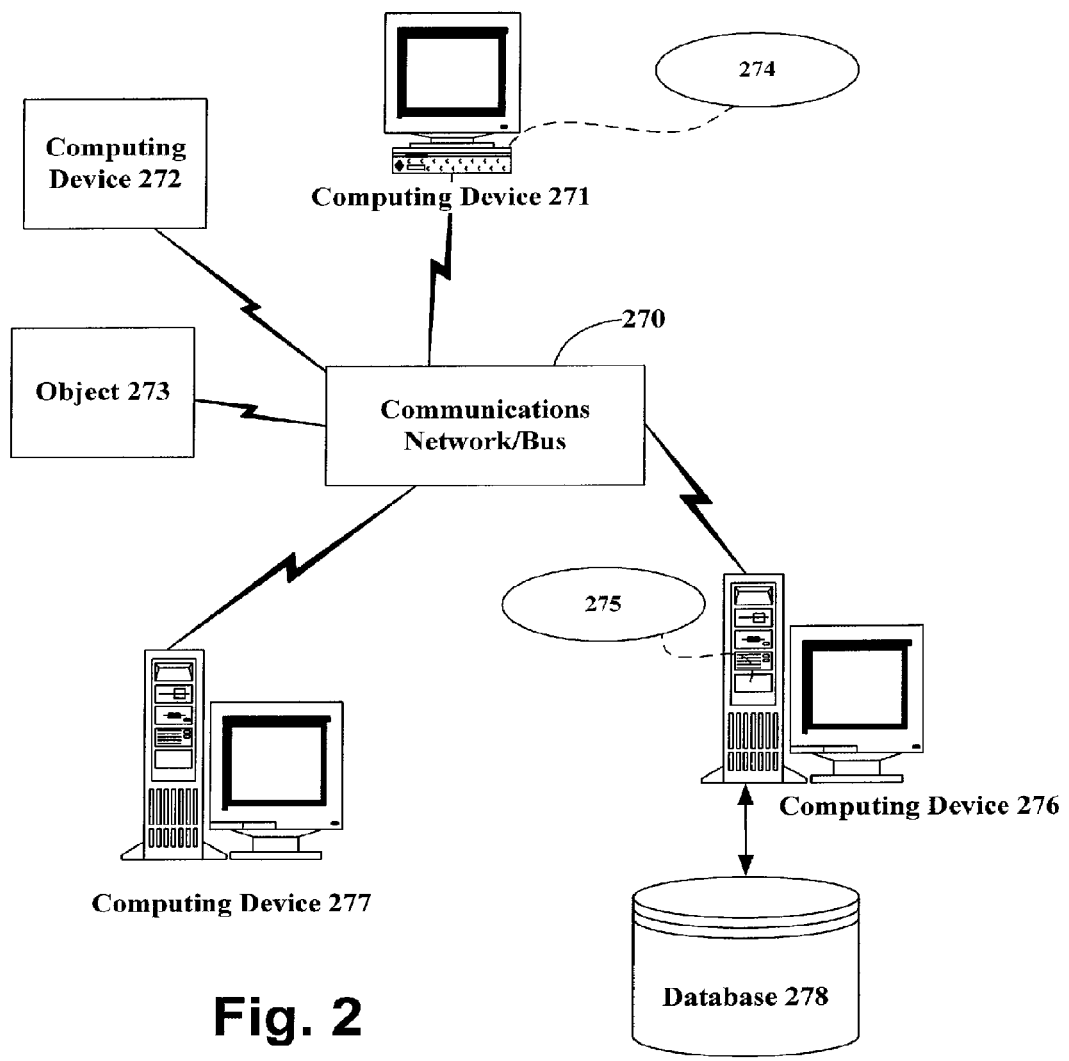
FIG. 2 illustrates an exemplary networked computing environment in which many computerized processes may be implemented to provide a life insurance underwriting risk calculator.

Referring next to FIG. 2, shown is an exemplary networked computing environment in which many computerized processes may be implemented to perform the processes described above. For example, parallel computing may be part of such a networked environment with various clients on the network of FIG. 2 using and/or implementing a life insurance underwriting risk calculator. One of ordinary skill in the art can appreciate that networks can connect any computer or other client or server device, or other devices in a distributed computing environment. In this regard, any computer system or environment having any number of processing, memory, or storage units, and any number of applications and processes occurring simultaneously is considered suitable for use in connection with the systems and methods provided.

Distributed computing provides sharing of computer resources and services by exchange between computing devices and systems. These resources and services include the exchange of information, cache storage, and disk storage for files. Distributed computing takes advantage of network connectivity, allowing clients to leverage their collective power to benefit the entire enterprise. In this regard, a variety of devices may have applications, objects, or resources that may implicate the processes described herein.

FIG. 2 provides a schematic diagram of an exemplary networked or distributed computing environment. The environment comprises computing devices 271, 272, 276, and 277 as well as objects 273, 274, and 275, and database 278. Each of these entities 271, 272, 273, 274, 275, 276, 277, and 278 may comprise or make use of programs, methods, data stores, programmable logic, etc. The entities 271, 272, 273, 274, 275, 276, 277, and 278 may span portions of the same or different devices such as PDAs, audio/video devices, MP3 players, personal computers, etc. Each entity 271, 272, 273, 274, 275, 276, 277, and 278 can communicate with another entity 271, 272, 273, 274, 275, 276, 277, and 278 by way of the communications network 270. In this regard, any entity may be responsible for the maintenance and updating of a database 278 or other storage element.

This network 270 may itself comprise other computing entities that provide services to the system of FIG. 2, and it may itself represent multiple interconnected networks. In accordance with an aspect of the inventive subject matter, each entity 271, 272, 273, 274, 275, 276, 277, and 278 may contain discrete functional program modules that might make use of an API, or other object, software, firmware, and/or hardware, to request services of one or more of the other entities 271, 272, 273, 274, 275, 276, 277, and 278.

It can also be appreciated that an object, such as 275, may be hosted on another computing device 276. Thus, although the physical environment depicted may show the connected devices as computers, such illustration is merely exemplary, and the physical environment may alternatively be depicted or described comprising various digital devices such as PDAs, televisions, MP3 players, etc., software objects such as interfaces, COM objects, and the like.

There are a variety of systems, components, and network configurations that support distributed computing environments. For example, computing systems may be connected together by wired or wireless systems, by local networks, or by widely distributed networks. Currently, many networks are coupled to the Internet, which provides an infrastructure for widely distributed computing and encompasses many different networks. Any such infrastructures, whether coupled to the Internet or not, may be used in conjunction with the systems and methods provided.

A network infrastructure may enable a host of network topologies such as client/server, peer-to-peer, or hybrid architectures. The "client" is a member of a class or group that uses the services of another class or group to which it is not related. In computing, a client is a process, i.e., roughly a set of instructions or tasks, that requests a service provided by another program. The client process utilizes the requested service without having to "know" any working details about the other program or the service itself. In a client/server architecture, particularly a networked system, a client is usually a computer that accesses shared network resources provided by another computer, e.g., a server. In the example of FIG. 2, any entity 271, 272, 273, 274, 275, 276, 277, and 278 can be considered a client, a server, or both, depending on the circumstances.

A server is typically, though not necessarily, a remote computer system accessible over a remote or local network, such as the Internet. The client process may be active in a first computer system, and the server process may be active in a second computer system, communicating with one another over a communications medium, thus providing distributed functionality and allowing multiple clients to take advantage of the information-gathering capabilities of the server. Any software objects may be distributed across multiple computing devices or objects.

Client(s) and server(s) may communicate with one another utilizing the functionality provided by protocol layer(s). For example, HyperText Transfer Protocol (HTTP) is a common protocol that is used in conjunction with the World Wide Web (WWW), or "the Web." Typically, a computer network address such as an Internet Protocol (IP) address or other reference such as a Universal Resource Locator (URL) can be used to identify the server or client computers to each other. The network address can be referred to as a URL address. Communication can be provided over a communications medium, e.g., client(s) and server(s) may be coupled to one another via TCP/IP connection(s) for high-capacity communication.

In light of the diverse computing environments that may be built according to the general framework provided in FIG. 2 and the further diversification that can occur in computing in a network environment such as that of FIG. 2, the systems and methods provided herein cannot be construed as limited in any way to a particular computing architecture or operating system. Instead, the inventive subject matter should not be limited to any single embodiment, but rather it should be construed in breadth and scope in accordance with the appended claims.

Some embodiments may include a medical diagnosis interpretation calculator (MDIC), including perhaps an electrocardiographic interpretation calculator (EIC). The calculator may interpret diagnoses and medical information bureau codes and may assign risk classes. The risk classes may be used for insurance underwriting, perhaps obviating a need for review of an application file by a medical director. The MDIC may enable an underwriter to independently and accurately interpret an electrocardiogram or other diagnostic evidence, to derive a diagnosis and a MIB code, and to assign a correct risk class to an application for insurance. Improved efficiency, decreased file transfers, decreased processing delays, and increased consistency among underwriters may result. Disclosed embodiments may thus decrease insurance processing time, and may result in better utilization of medical director skills and knowledge.

Figure 3:
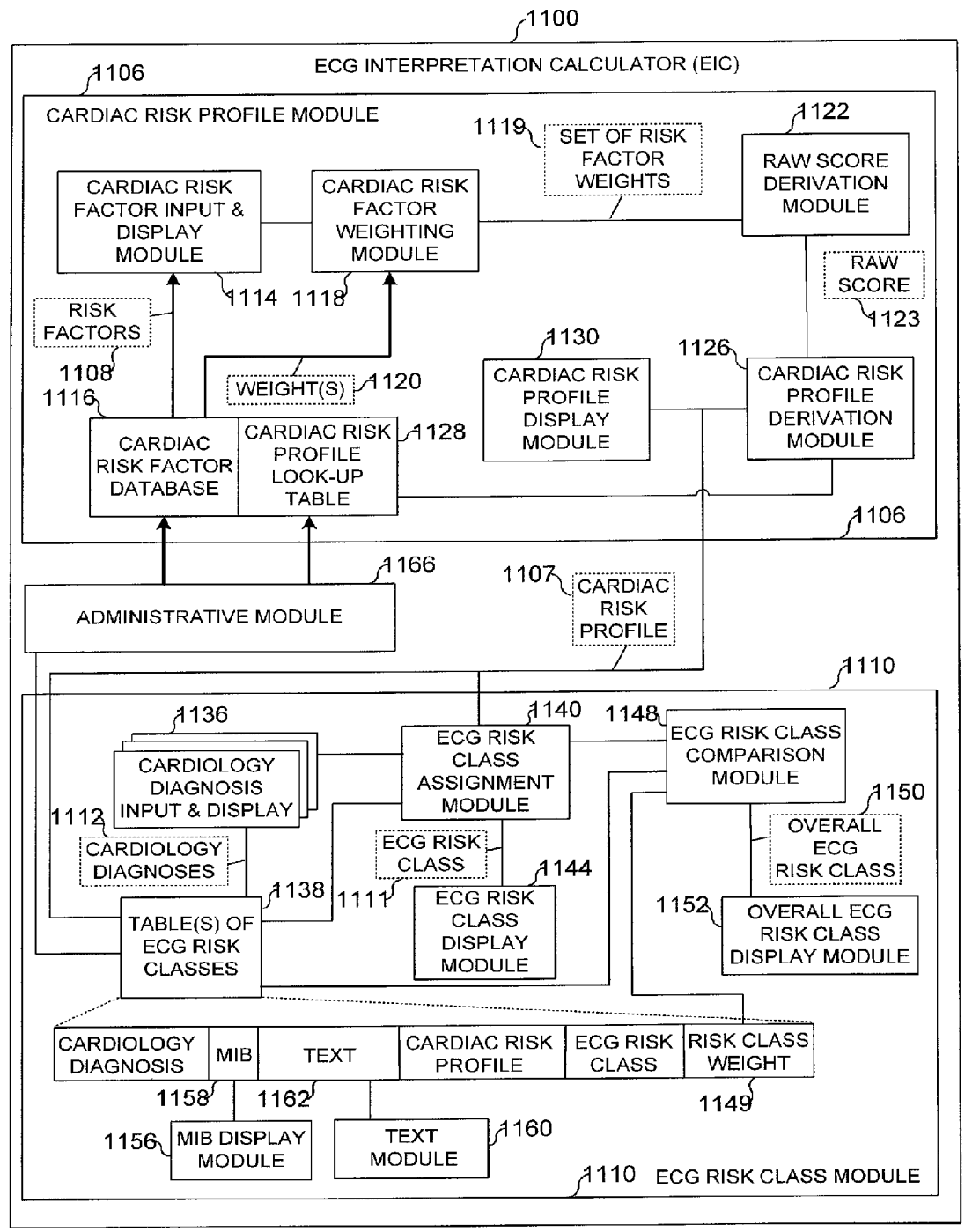
FIG. 3 is a block diagram of an electrocardiographic interpretation calculator according to various embodiments.

FIG. 3 is a block diagram of an electrocardiographic interpretation calculator EIC 1100 according to various embodiments. The EIC 1100 may include a cardiac risk profile module 1106 to derive a cardiac risk profile 1107 from a plurality of cardiac risk factors 1108. An ECG risk class module 1110 may be coupled to the cardiac risk profile module 1106 to derive one or more ECG risk classes 1111 from one or more cardiology diagnoses 1112 weighted by the cardiac risk profile 1107. A resulting overall ECG risk class 1150 may be used to perform an insurance underwriting function.

The cardiac risk profile module 1106 may include a cardiac risk factor input and display module 1114. The cardiac risk factor input and display module 1114 may accept an input of the plurality of cardiac risk factors 1108, a selection of the plurality of cardiac risk factors from a displayed list of cardiac risk factors, or both. The displayed list of cardiac risk factors may be retrieved from a risk factor database 1116.

A cardiac risk factor weighting module 1118 may be coupled to the cardiac risk factor input and display module 1114. The cardiac risk factor weighting module 1118 may assign a weight 1119 to each member of the set of cardiac risk factors to obtain a set of cardiac risk factor weights 1120. A raw score derivation module 1122 may be coupled to the cardiac risk factor weighting module 1118. The raw score derivation module 1122 may perform a mathematical function on the set of cardiac risk factor weights 1120 to obtain a cardiac risk factor raw score 1123.

The EIC 1100 may also include a cardiac risk profile derivation module 1126 coupled to the raw score derivation module 1122. The cardiac risk profile derivation module 1126 may derive the cardiac risk profile 1107 from the cardiac risk factor raw score 1123. In some embodiments, the cardiac risk profile 1107 may be derived by indexing the cardiac risk profile 1107 from a look-up table of cardiac risk profiles 1128 using the cardiac risk factor raw score 1123 as an index value.

The cardiac risk profile 1107 may also be derived by selecting a cardiac risk profile associated with a range of cardiac risk factor raw scores wherein the cardiac risk factor raw score 1123 falls within the range of cardiac risk factor raw scores. A third way of deriving the cardiac risk profile 1107 may include performing a mathematical function on the cardiac risk factor raw score 1123. The aforementioned methods of deriving the cardiac risk profile 1107 may be used singly or in any combination. Other methods of deriving the cardiac risk profile 1107 may be possible. A cardiac risk profile display module 1130 may be coupled to the cardiac risk profile derivation module 1126 to display the cardiac risk profile 1107.

The ECG risk class module 1110 may also include a cardiology diagnosis input and display module 1136. The cardiology diagnosis input and display module 1136 may accept an input of the cardiology diagnos(es) 1112, a selection of the cardiology diagnos(es) 1112 from one or more displayed list(s) of cardiology diagnoses, or both. The displayed list(s) of cardiology diagnoses may be retrieved from one or more tables of ECG risk classes 1138.

A risk class assignment module 1140 may be coupled to the cardiology diagnosis input and display module 1136. The risk class assignment module 1140 may look up the ECG risk class(es) 1111 from the table(s) of ECG risk classes 1138. A risk class look-up operation may use the cardiac risk profile 1107 and the cardiology diagnos(es) 1112. The table(s) of ECG risk classes 1138 may associate the ECG risk class(es) 1111, the cardiac risk profile 1107, and the cardiology diagnos(es) 1112. An ECG risk class display module 1144 may be coupled to the risk class assignment module 1140 to display the ECG risk class(es) 1111.

The EIC 1100 may further include an ECG risk class comparison module 1148 coupled to the risk class assignment module 1140. The ECG risk class comparison module 1148 may associate an ECG risk class weight 1149 with each of the ECG risk class(es) 1111. The ECG risk class comparison module 1148 may also derive the overall ECG risk class 1150 from the ECG risk class(es) 1111. The overall ECG risk class 1150 may be derived by selecting an ECG risk class of greatest weight from the ECG risk class(es) 1111. A greater weight is associated with a higher level of underwriting risk.

The overall ECG risk class 1150 may also be derived by performing a mathematical function on the ECG risk class weight(s) 1149 to yield an overall ECG risk class index. The overall ECG risk class index may be used to index the overall ECG risk class from the table(s) of ECG risk classes 1138. An overall ECG risk class display module 1152 may display the overall ECG risk class 1150.

Other information associated with the cardiology diagnos(es) 1112 may be displayed. A MIB display module 1156 may be coupled to the table(s) of ECG risk classes 1138. The MIB display module 1156 may extract a MIB code 1158 associated with the cardiology diagnos(es) 1112 from the table(s) of ECG risk classes 1138 and may display the MIB code 1158. A text module 1160 may be coupled to the table(s) of ECG risk classes 1138. The text module 1160 may extract a field of explanatory text 1162 associated with the cardiology diagnos(es) 1112 from the table(s) of ECG risk classes 1138. The text module 1160 may also display the field of explanatory text 1162.

The EIC 1100 may further include an administrative module 1166 coupled to the cardiac risk profile module 1106 and to the ECG risk class module 1110. The administrative module 1166 may be used to populate the risk factor database 1116 associated with the displayed list of cardiac risk factors, to modify the look-up table of cardiac risk profiles 1128, and to modify the table(s) of EGG risk classes 1138.

Figure 4:
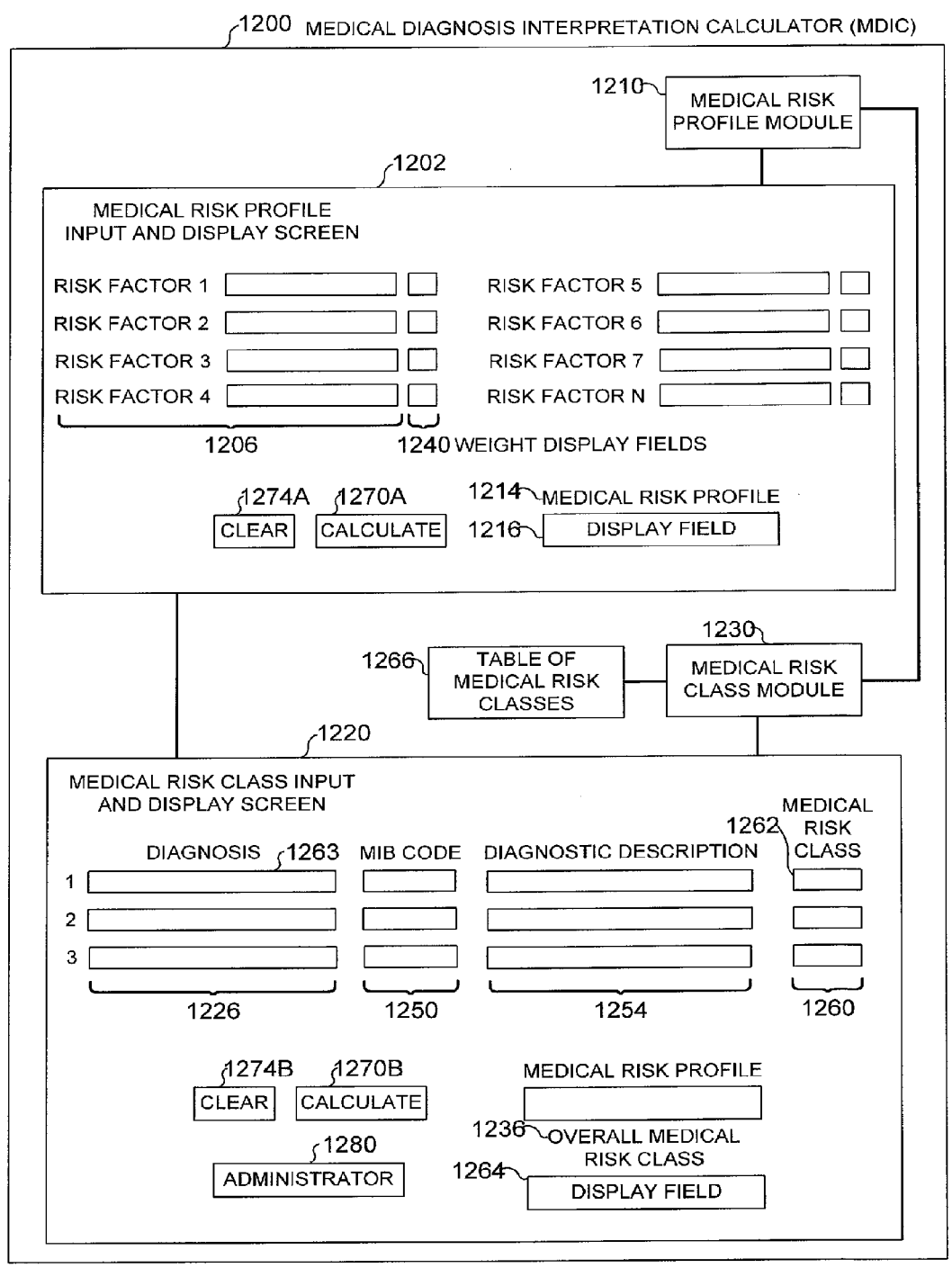
FIG. 4 is a block diagram of a medical diagnosis interpretation calculator according to various embodiments.

FIG. 4 is a block diagram of a medical diagnosis interpretation calculator (MDIC) 1200 according to various embodiments. The MDIC 1200 may include a medical risk profile input and display device 1202 to enter a plurality of medical risk factors 1206. A medical risk profile module 1210 may be coupled to the medical risk profile input and display device 1202. The medical risk profile module 1210 may operate to derive a medical risk profile 1214 from the plurality of medical risk factors 1206. A medical risk profile display field 1216 may display the medical risk profile 1214 on the medical risk profile input and display device 1202.

The MDIC 1200 may also include a plurality of weight display fields 1240 associated with the medical risk profile input and display device 1202. Each weight display field may display a numerical weighting factor associated with one of the plurality of medical risk factors 1206. Each one of the plurality of weight display fields 1240 may comprise a read-only field unless the MDIC 1200 is operating in an administrative mode.

A medical risk class input and display device 1220 may be communicatively coupled to the medical risk profile input and display device 1202 to enter one or more medical diagnoses 1226. A medical risk class module 1230 may be coupled to the medical risk profile module 1210 and to the medical risk class input and display device 1220 to derive an overall medical risk class 1236 from the medical diagnos(es) 1226 weighted by the medical risk profile 1214.

One or more MIB code display fields 1250 may be associated with the medical risk class input and display device 1220. Each MIB code display field may be associated with one of the medical diagnos(es) 1226 to display the corresponding MIB code. The medical risk class input and display device 1220 may also include one or more explanatory text display fields 1254 to provide a short description of the medical diagnos(es) 1226.

The MDIC 1200 may also include one or more medical risk class display fields 1260 associated with the medical risk class input and display device 1220. Each of the medical risk class display field(s) 1260 may be associated with one of the medical diagnos(es) 1226. For example, a medical risk class display field 1262 may display a medical risk class derived from a medical diagnosis 1263 weighted by the medical risk profile 1214.

An overall medical risk class display field 1264 may be associated with the medical risk class input and display device 1220 to display the overall medical risk class 1236. The overall medical risk class 1236 may be derived by selecting a medical risk class (e.g., from the medical risk class display field(s) 1260) of highest risk. The overall medical risk class 1236 may also be derived by performing a mathematical function on a numerical weight associated with each medical risk class. The mathematical function may yield an overall medical risk class index to use to index the overall medical risk class from one or more table(s) of medical risk classes 1266.

The MDIC 1200 may also include one or more command devices 1270A and 1270B. The command device(s) 1270A and 1270B may be associated with the medical risk profile input and display device 1202 and with the medical risk class input and display device 1220, respectively. The command device 1270A may instruct the medical risk profile module 1210 to derive or to calculate the medical risk profile 1214. The command device 1270B may instruct the medical risk class module 1220 to derive or to calculate a medical risk class (e.g., a medical risk class displayed in the medical risk class display field 1262) from a medical diagnosis (e.g., from the medical diagnosis 1263). The command device 1270B may also instruct the medical risk class module 1220 to derive or to calculate the overall medical risk class 1236.

One or more entry reset devices 1274A and 1274B may operate to clear entries associated with the plurality of medical risk factors 1206 and with the medical diagnos(es) 1226, respectively. An administrator device 1280 may be associated with the medical risk profile input and display device, the medical risk class input and display device, or both. The administrator device 1280 may be used to perform a database maintenance function associated with the MDIC 1200. Embodiments of the medical risk profile input and display device 1202 and the medical risk class input and display device 1220 may include sets of switches, an electronic display, a computer screen, sets of drop-down menus, sets of fields to be filled in, sets of radio buttons, sets of check boxes, and/or a voice recognition system, among other input/output devices.

Figure 5:
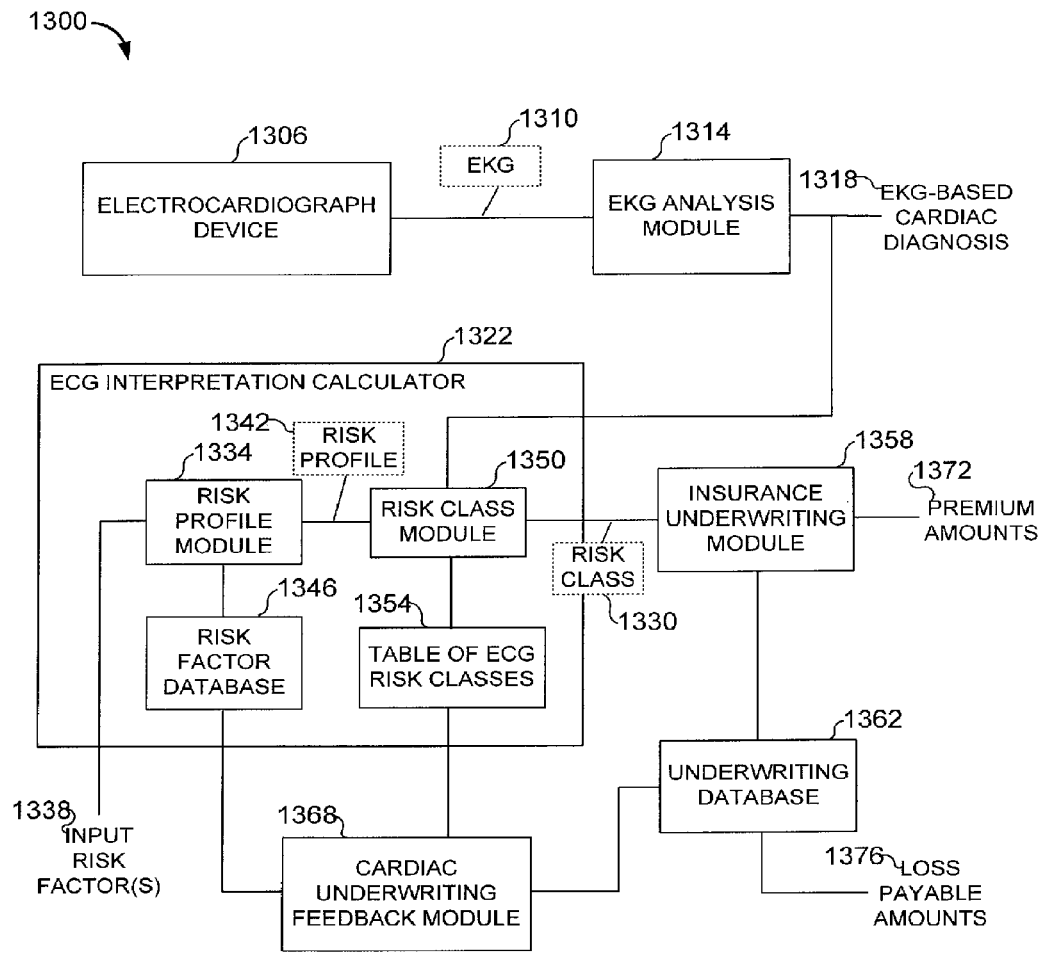
FIG. 5 is a block diagram of a system according to various embodiments.

FIG. 5 comprises a block diagram of a system 1300 according to various embodiments. The system 1300 may include one or more of the EIC 1100 and/or the MDIC 1200, as previously described. The system 1300 may also include an electrocardiograph device 1306 to produce an EKG 1310. An EKG analysis module 1314 may be coupled to the electrocardiograph device 1306 to receive the EKG 1310 from the electrocardiograph device 1306. The EKG analysis module 1314 may derive one or more cardiology diagnos(es) 1318 from the EKG 1310. The cardiology diagnos(es) 1318 may comprise a set of characteristics associated with an EKG waveform.

An ECG interpretation calculator 1322 may be coupled to the EKG analysis module 1314 to receive the cardiology diagnos(es) 1318. The ECG interpretation calculator 1322 may derive an ECG risk class 1330 responsive to a receipt of the cardiology diagnos(es) 1318.

The system 1300 may also include a cardiac risk profile module 1334 associated with the ECG interpretation calculator 1322. The cardiac risk profile module 1334 may receive a set of cardiac risk factors 1338 associated with an applicant for insurance. A service representative associated with an insurance company may input the set of cardiac risk factors 1338, for example. The cardiac risk profile module 1334 may derive a cardiac risk profile 1342 from the set of cardiac risk factors 1338. A numerical weight associated with each one of the set of cardiac risk factors 1338 may be adjusted by editing a risk factor database 1346 used to derive the cardiac risk profile 1342.

An ECG risk class module 1350 may be coupled to the cardiac risk profile module 1334 to derive the ECG risk class 1330 from the cardiology diagnos(es) 1318 and from the cardiac risk profile 1342. The ECG risk class 1330 may thus comprise the cardiology diagnos(es) 1318 weighted by the cardiac risk profile 1342. A table of ECG risk classes 1354 may be coupled to the ECG risk class module 1350 to associate the ECG risk class 1330, the cardiology diagnos(es) 1318, and the cardiac risk profile 1342.

The system 1300 may also include an insurance underwriting module 1358 coupled to the ECG interpretation calculator 1322. The insurance underwriting module 1358 may receive the ECG risk class 1330 from the ECG interpretation calculator 1322 and may cause an insurance underwriting function to be performed using the ECG risk class 1330. An underwriting database 1362 may be coupled to the underwriting module 1358 to store historical relationships among insurance risk classes (e.g., the ECG risk class 1330), insurance premiums, and losses payable.

A cardiac underwriting feedback module 1368 may be coupled to the table of ECG risk classes 1354 and to the risk factor database 1346. The cardiac underwriting feedback module 1368 may adjust one or more entries in the table of ECG risk classes 1354 and/or in the risk factor database 1346. The entries may be adjusted such that a cumulative premium amount output 1372 of the insurance underwriting system summed over a first selectable period of time divided by a cumulative loss payment amount input 1376 to the underwriting database summed over a second selectable period of time approaches a target value. Other financial ratio objectives may be targeted using disclosed embodiments.

Any of the components previously described can be implemented in a number of ways, including embodiments in software. Thus, the EIC 1100; cardiac risk profile module 1106; cardiac risk profile 1107; cardiac risk factors 1108; ECG risk class module 1110; ECG risk class(es) 1111; cardiology diagnos(es) 1112; cardiac risk factor input and display module 1114; risk factor database 1116; cardiac risk factor weighting module 1118; cardiac risk factor weights 1119, 1120; raw score derivation module 1122; cardiac risk factor raw score 1123; cardiac risk profile derivation module 1126; look-up table of cardiac risk profiles 1128; cardiac risk profile display module 1130; cardiology diagnosis input and display module 1136; table(s) of ECG risk classes 1138; risk class assignment module 1140; ECG risk class display module 1144; ECG risk class comparison module 1148; ECG risk class weight 1149; overall ECG risk class 1150; overall ECG risk class display module 1152; MIB display module 1156; MIB code 1158; text module 1160; field of explanatory text 1162; administrative module 1166; MDIC 1200; medical risk profile input and display device 1202; medical risk factor(s) 1206; medical risk profile module 1210; medical risk profile 1214; medical risk profile display field 1216; medical risk class input and display device 1220; weight display fields 1240; medical diagnoses 1226, 1263; medical risk class module 1230; overall medical risk class 1236; MIB code display field(s) 1250; explanatory text display field(s) 1254; medical risk class display field(s) 1260, 1262; overall medical risk class display field 1264; table(s) of medical risk classes 1266; command device(s) 1270A, 1270B; entry reset device(s) 1274A, 1274B; administrator device 1280; system 1300; electrocardiograph device 1306; electrocardiogram (EKG) 1310; EKG analysis module 1314; cardiology diagnos(es) 1318; ECG interpretation calculator 1322; ECG risk class 1330; cardiac risk profile module 1334; cardiac risk factors 1338; cardiac risk profile 1342; risk factor database 1346; ECG risk class module 1350; table of ECG risk classes 1354; insurance underwriting module 1358; underwriting database 1362; cardiac underwriting feedback module 1368; premium amounts output 1372; and loss payment amounts input 1376 may all be characterized as "modules" herein.

The modules may include hardware circuitry, single or multi-processor circuits, memory circuits, software program modules and objects, firmware, and combinations thereof, as desired by the architect of the EIC 1100, the MDIC 1200, and the system 1300 and as appropriate for particular implementations of various embodiments.

The apparatus and systems of various embodiments can be used in applications other than deriving a risk class associated with an application for insurance using a medical interpretation calculator to interpret an electrocardiogram or other diagnostic evidence. Thus, various embodiments are not to be so limited. The illustrations of the EIC 1100, the MDIC 1200, and the system 1300 are intended to provide a general understanding of the structure of various embodiments. They are not intended to serve as a complete description of all the elements and features of apparatus and systems that might make use of the structures described herein.

Some embodiments may include a number of methods.

Figure 6:
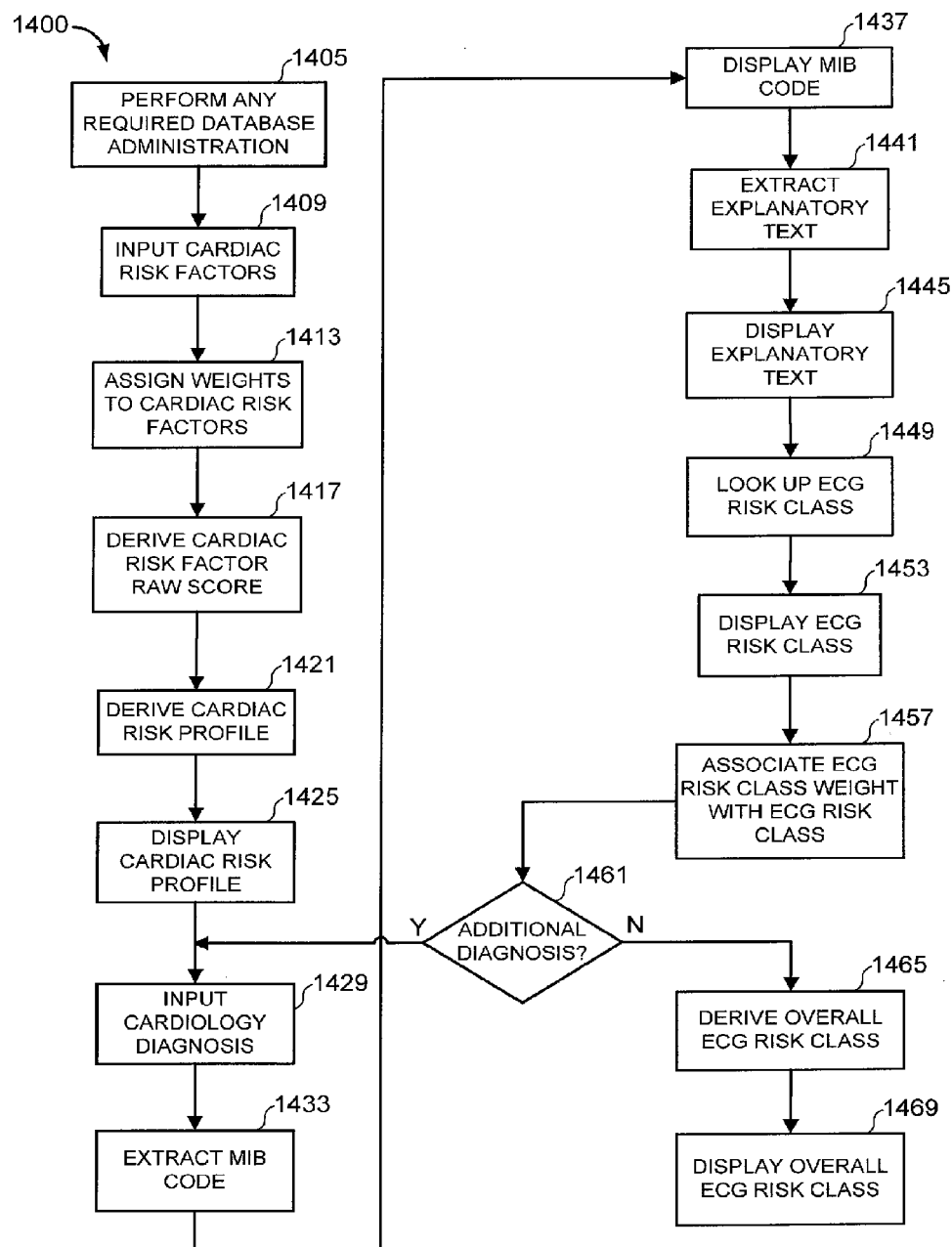
FIGS. 6-8 are flow diagrams illustrating several methods according to various embodiments.

FIG. 6 is a flow diagram illustrating several methods according to various embodiments. Some embodiments may use an ECG interpretation calculator (EIC) to derive an ECG risk class from one or more cardiology diagnoses, as previously described. Referring back to FIG. 3, for example, the EIC 1100 may be used to derive the ECG risk class. Each diagnosis may be weighted by a plurality of cardiac risk factors. The plurality of cardiac risk factors may comprise a cardiac risk profile.

Embodiments disclosed herein may include tables and databases associated with the EIC 1100. A method 1400 may begin at block 1405 with performing any required database administration functions associated with the tables and databases using an administrative module associated with the EIC 1100. The database administration functions may include populating a risk factor database associated with a displayed list of cardiac risk factors. Other database administration functions may include modifying one or more tables of ECG risk classes and/or a look-up table of cardiac risk profiles.

The method 1400 may continue with accepting an input of a plurality of cardiac risk factors, at block 1409. In some embodiments, the input operation may comprise selecting the plurality of cardiac risk factors from a list of cardiac risk factors displayed at the EIC 1100. The displayed list of cardiac risk factors may be read from a risk factor database. A weight may be assigned to each member of the set of cardiac risk factors to obtain a set of cardiac risk factor weights, at block 1413. A mathematical function may be performed on the set of cardiac risk factor weights to derive a cardiac risk factor raw score, at block 1417.

The method 1400 may further include deriving a cardiac risk profile from the cardiac risk factor raw score, at block 1421. In some embodiments, the cardiac risk profile may be indexed from a look-up table of cardiac risk profiles using the cardiac risk factor raw score as an index value. The cardiac risk profile may also be selected as being associated with a particular range of cardiac risk factor raw scores. That is, the cardiac risk factor raw score may fall within the particular range of cardiac risk factor raw scores. The cardiac risk profile may also be derived by performing a mathematical function on the cardiac risk factor raw score. The cardiac risk profile may be displayed, at block 1425.

The method 1400 may also include accepting a cardiology diagnosis input, at block 1429. The cardiology diagnosis may be input directly, or may be selected from one or more displayed lists of cardiology diagnoses at the EIC 1100. The displayed list(s) of cardiology diagnoses may be read from one or more tables of ECG risk classes.

The method 1400 may continue at block 1433 with extracting a MIB code associated with the cardiology diagnosis from the table(s) of ECG risk classes. The MIB code may be displayed, at block 1437. A field of explanatory text associated with the cardiology diagnosis may be extracted from the table(s) of ECG risk classes, at block 1441. The field of explanatory text may be displayed, at block 1445.

The method 1400 may also include looking up an ECG risk class, at block 1449. The ECG risk class may be extracted from the table(s) of ECG risk classes, using perhaps the cardiac risk profile and the at least one cardiology diagnosis. Thus, the table(s) of ECG risk classes may associate the ECG risk class, the cardiac risk profile, and the cardiology diagnosis. The method 1400 may also include displaying the ECG risk class, at block 1453. The method 1400 may further include associating an ECG risk class weight with the ECG risk class, at block 1457. Activities associated with blocks 1429 through 1457 may be repeated to accept two or more cardiology diagnoses, to display information related to the cardiology diagnoses, and to look up an ECG risk class and weight assigned to each cardiology diagnosis. The method 1400 may include a decision block 1461 to enable an input and processing of multiple cardiology diagnoses.

The method 1400 may continue at block 1465 with deriving an overall ECG risk class from the ECG risk class(es). The overall ECG risk class may be selected to be equal to the ECG risk class of greatest weight, wherein the greatest weight corresponds to an ECG risk class of highest risk. The overall ECG risk class may also be derived by performing a mathematical function on the ECG risk class weight associated with each ECG risk class to yield an overall ECG risk class index. The overall ECG risk class index may then be used to index the overall ECG risk class from the table(s) of ECG risk classes. The method 1400 may conclude at block 1469 with displaying the overall ECG risk class. Other methods may be possible.

Figure 7:
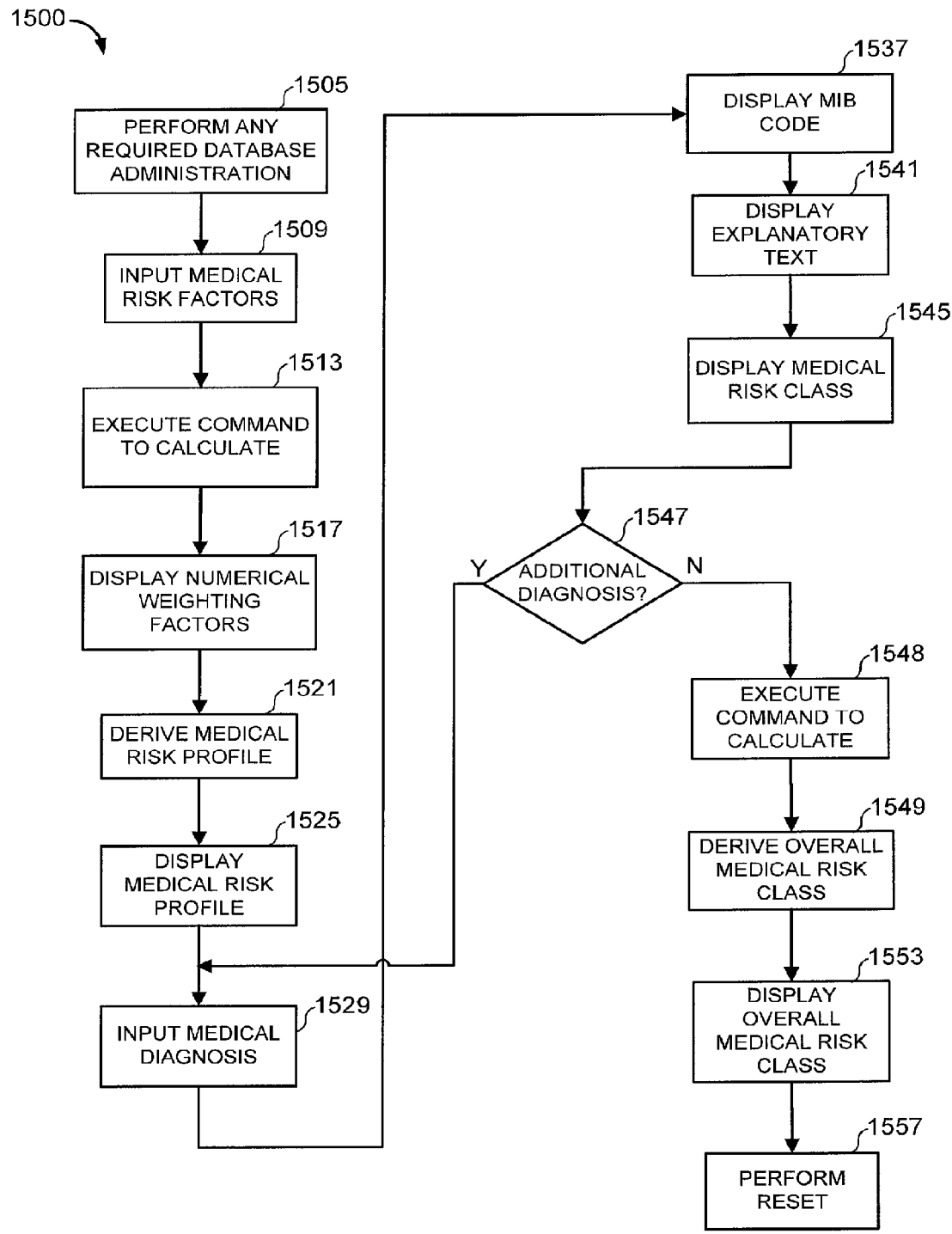

FIG. 7 is a flow diagram illustrating several methods according to various embodiments. A method 1500 may begin at block 1505 with performing any required database maintenance function associated with a medical diagnosis interpretation calculator (MDIC) using an administrator device. The method 1500 may continue at block 1509 with entering a plurality of medical risk factors into the MDIC using a medical risk profile input and display device. A medical risk profile module may be commanded to derive the medical risk profile, at block 1513.

The method 1500 may also include displaying a numerical weighting factor associated with each one of the plurality of medical risk factors, at block 1517. The numerical weighting factors may be displayed using a plurality of weight display fields associated with the medical risk profile input and display device. Each weight display field may comprise a read-only field unless the MDIC is operating in an administrative mode.

The method 1500 may further include deriving a medical risk profile from the plurality of medical risk factors, at block 1521. The medical risk profile may be derived using a medical risk profile module coupled to the medical risk profile input and display device. The medical risk profile may be displayed using a medical risk profile display field associated with the medical risk profile input and display device, at block 1525.

The method 1500 may continue at block 1529 with entering a medical diagnosis using a medical risk class input and display device communicatively coupled to the medical risk profile input and display device. A MIB code associated with the at least one medical diagnosis may be displayed using a MIB code display field associated with the medical risk class input and display device, at block 1537. A short description of the medical diagnosis may be provided, at block 1541. The short description may be displayed using an explanatory text display field associated with the medical risk class input and display device.

The method 1500 may also include displaying a medical risk class derived from the medical diagnosis weighted by the medical risk profile, at block 1545. The medical risk class may be displayed using a medical risk class display field associated with the medical risk class input and display device. In some embodiments, more than one medical diagnosis may be entered into the MDIC, using the activities of blocks 1529 through 1547. In the case of multiple medical diagnoses, multiple medical risk class display fields may be associated one for one with the medical diagnoses.

The method 1500 may continue at block 1548 with commanding the medical risk class module to derive the medical risk class and/or the overall medical risk class. A command device associated with the medical risk class input and display device may be used for this purpose. An overall medical risk class may be derived from the medical diagnos(es) weighted by the medical risk profile, at block 1549. A medical risk class module may be coupled to the medical risk profile module and to the medical risk class input and display device to accomplish this purpose.

The overall medical risk class may be derived by selecting a medical risk class of highest risk. The overall medical risk class may also be derived by performing a mathematical function on a numerical weight associated with each medical risk class to yield an overall medical risk class index, as previously described. The resulting overall medical risk class index may be used to index the overall medical risk class from one or more tables of medical risk classes.

The overall medical risk class may be displayed using an overall medical risk class display field associated with the medical risk class input and display device, at block 1553. The method 1500 may conclude with resetting entries associated with the plurality of medical risk factors and with the medical diagnos(es) using an entry reset device, at block 1557.

It is noted that the medical risk profile input and display device, the medical risk class input and display device, or both may comprise a set of switches, an electronic display, a computer screen, a set of drop-down menus, a set of fields to be filled in, a set of radio buttons, a set of check boxes, and/or a voice recognition system, in any combination. Additional methods may be possible.

Figure 8:
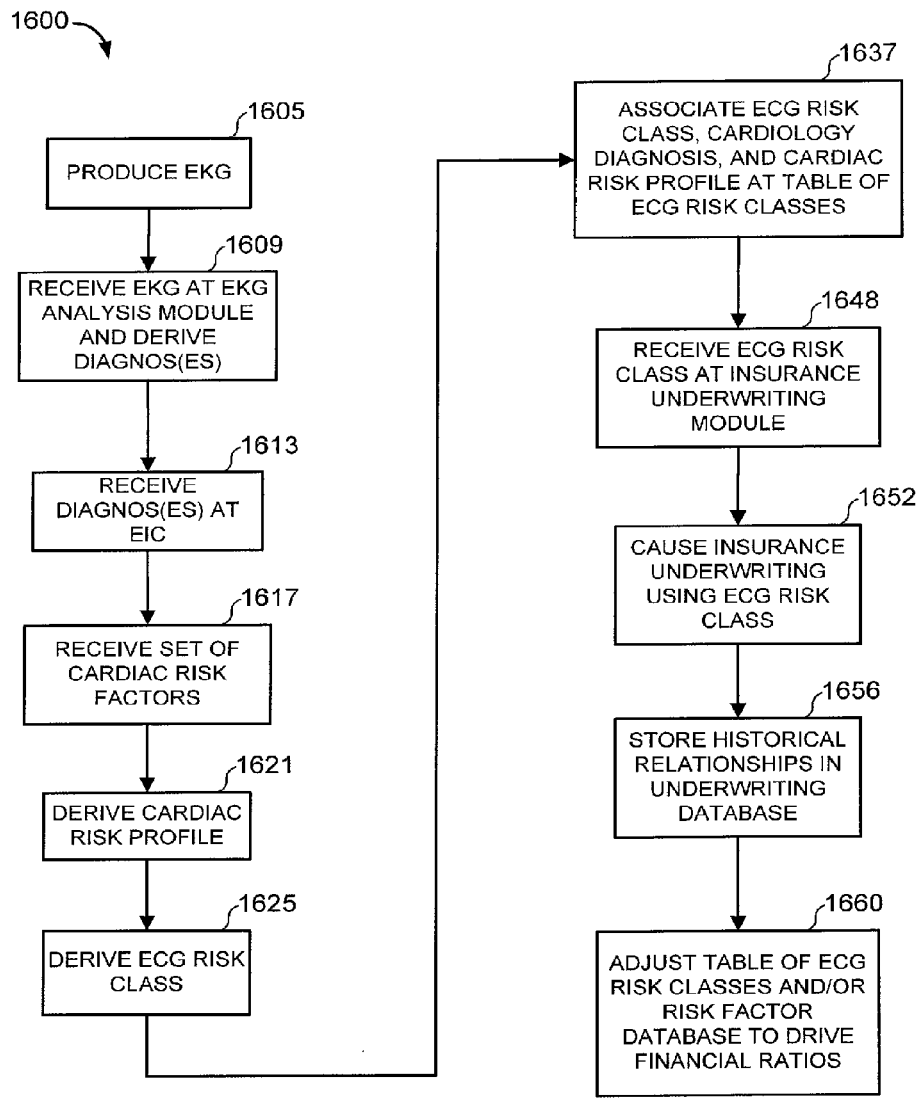

FIG. 8 is a flow diagram illustrating several methods according to various embodiments. A method 1600 may begin at block 1605 with producing an EKG using an electrocardiograph device. The electrocardiograph device may be capable of producing a digital representation of the EKG. The method 1600 may continue at block 1609 with receiving the EKG at an EKG analysis module coupled to the electrocardiograph device and deriving one or more cardiology diagnoses from the EKG. The cardiology diagnos(es) may comprise a set of characteristics associated with an EKG waveform.

The method 1600 may also include receiving the cardiology diagnos(es) at an EIC coupled to the EKG analysis module, at block 1613. The method 1600 may continue at block 1617 with receiving a set of cardiac risk factors associated with an applicant for insurance. The set of cardiac risk factors may be received at a cardiac risk profile module within the ECG interpretation calculator. A cardiac risk profile may be derived from the set of cardiac risk factors, at block 1621. A numerical weight associated with each one of the set of cardiac risk factors may be adjustable by editing a risk factor database used to derive the cardiac risk profile.

The method 1600 may further include deriving an ECG risk class responsive to the receipt of the cardiology diagnos(es), at block 1625. The ECG risk class may comprise the cardiology diagnos(es) weighted by the cardiac risk profile. The ECG risk class may be derived from the cardiology diagnos(es) and from the cardiac risk profile using an ECG risk class module coupled to the cardiac risk profile module. The method 1600 may also include associating the ECG risk class, the at least one cardiology diagnosis, and the cardiac risk profile, at block 1637. A table of ECG risk classes coupled to an ECG risk class module may be used in the association operation.

The method 1600 may also include receiving the ECG risk class at an insurance underwriting module coupled to the ECG interpretation calculator, at block 1648. The method 1600 may cause an insurance underwriting function to be performed using the ECG risk class, at block 1652.

In some embodiments, the method 1600 may include storing historical relationships between insurance risk classes, insurance premiums, and/or losses payable using an underwriting database coupled to the underwriting module, at block 1656. An iteration of the method 1600 may conclude at block 1660 with adjusting one or more entries in the table of ECG risk classes and/or in the risk factor database. The entries may be adjusted using a cardiac underwriting feedback module coupled to the table of ECG risk classes and to the risk factor database. The tables may be adjusted to drive one or more financial ratios to desired goals. For example, the tables may be adjusted such that a cumulative amount of premiums calculated by the insurance underwriting module summed over a first selectable period of time divided by a cumulative amount of losses payable associated with the cumulative amount of premiums approaches a target value.

It may be possible to execute the activities described herein in an order other than the order described. And, various activities described with respect to the methods identified herein can be executed in repetitive, serial, or parallel fashion.

A software program may be launched from a computer-readable medium in a computer-based system to execute functions defined in the software program. Various programming languages may be employed to create software programs designed to implement and perform the methods disclosed herein. The programs may be structured in an object-orientated format using an object-oriented language such as Java or C++. Alternatively, the programs may be structured in a procedure-orientated format using a procedural language, such as assembly or C. The software components may communicate using a number of mechanisms well known to those skilled in the art, such as application program interfaces or inter-process communication techniques, including remote procedure calls. The teachings of various embodiments are not limited to any particular programming language or environment. Thus, other embodiments may be realized, as discussed regarding FIG. 13 further below.

Life Insurance Underwriting Risk Calculator

Some embodiments may include a Life Insurance Underwriting Risk Calculator. The Life Insurance Underwriting Risk Calculator is a tool that may be used for insurance underwriting, perhaps obviating a need for review and/or reconsideration of an application file by a medical director. The Life Insurance Underwriting Risk Calculator may comprise a plurality of subsystems or modules, each of which in itself may comprise a calculator for a particular category of medical diagnoses.

Using the Life Insurance Underwriting Risk Calculator, an underwriter may independently determine whether an applicant could be granted a more preferential risk class, and if so, what further action(s) the applicant would have to satisfy to reach that risk class. In some embodiments, a medical director is involved in rate class determination to a substantially less degree than without the underwriters' utilization of this tool.

Improved efficiency, decreased file transfers, decreased processing delays, and increased consistency among underwriters may result. Disclosed embodiments may thus decrease insurance processing time, and may result in better utilization of medical director skills and knowledge.

Figure 9:
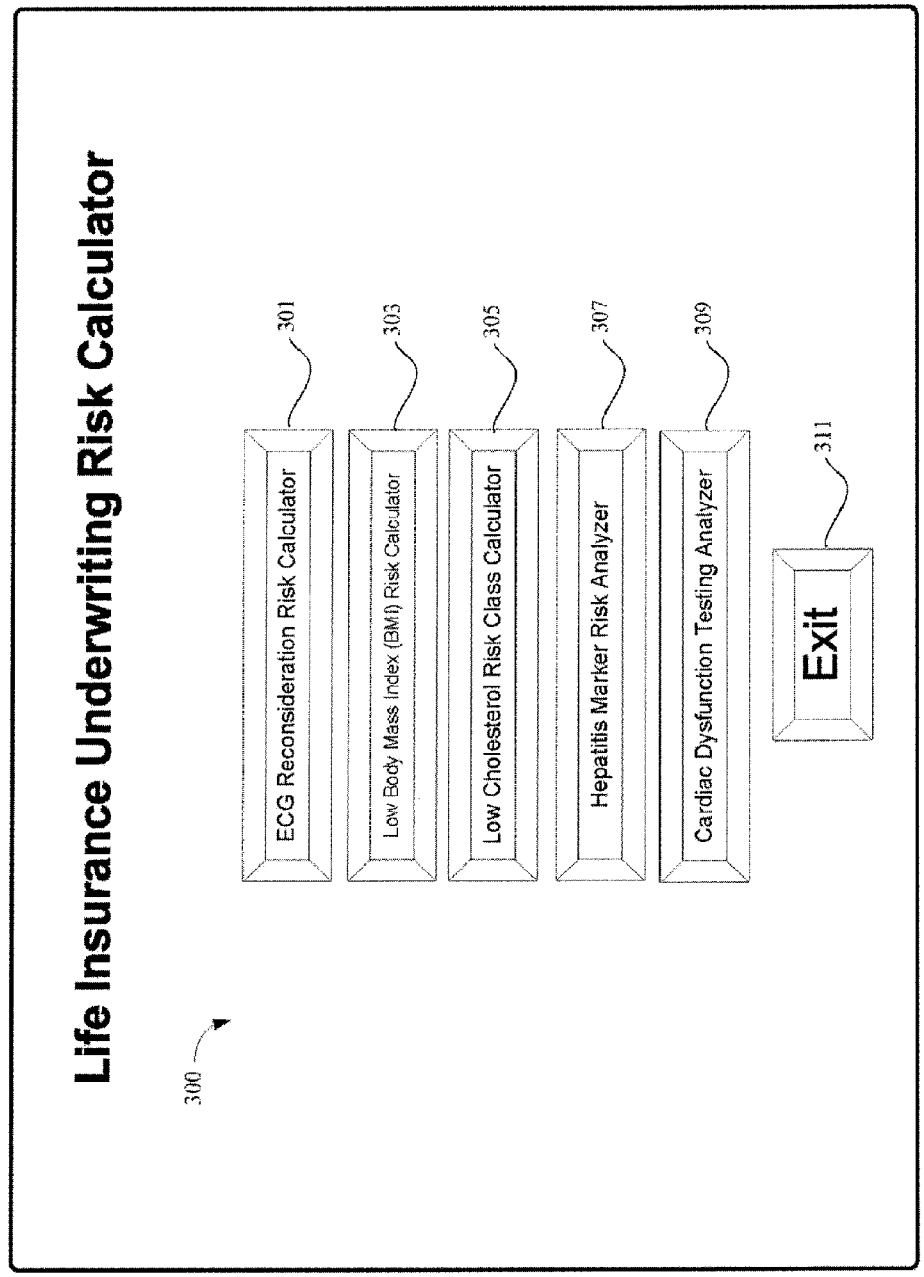
FIG. 9 is a diagram illustrating an graphical user interface of an example system comprising a life insurance underwriting risk calculator.

FIG. 9 is a diagram illustrating a graphical user interface of an example system comprising a Life Insurance Underwriting Risk Calculator 300. Shown is one main graphical interface having controls to start an ECG Reconsideration Risk Calculator 301, a Low Body Mass Index (BMI) Risk Calculator 303, a Low Cholesterol Risk Class Calculator 305, a Hepatitis Marker Risk Analyzer 307, a Cardiac Dysfunction Testing Analyzer 309, and an exit button 311.

The ECG Reconsideration Risk Calculator 301, Low Body Mass Index (BMI) Risk Calculator 303, Low Cholesterol Risk Class Calculator 305, Hepatitis Marker Risk Analyzer 307, and Cardiac Dysfunction Testing Analyzer 309 may form part of a more comprehensive automated insurance underwriting system that calculates risk (e.g. risk category) associated with issuance of a life insurance policy to an individual. In an embodiment, the system may comprise at least one subsystem that accepts risk criteria values to be entered, at least one subsystem that assigns at least one pre-determined risk category based upon the criteria values, and at least one subsystem that displays the at least one predetermined risk category. Other embodiments, comprising a plurality of subsystems and/or modules, are within the scope of the inventive subject matter.

Figure 10B:
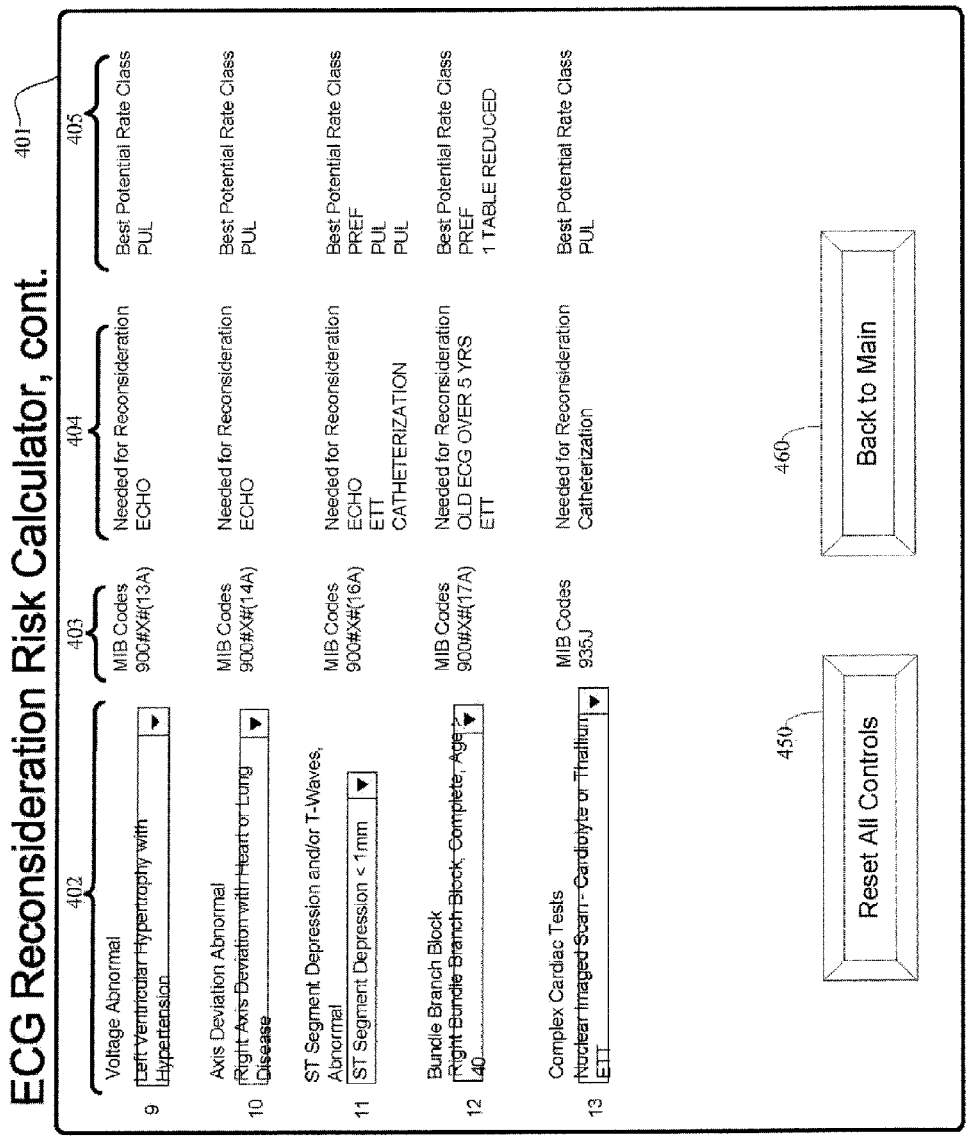

FIGS. 10A and 10B together constitute a graphical user interface of an example Electrocardiogram (ECG) Reconsideration Risk Calculator 401 portion of an example system comprising a Life Insurance Underwriting Risk Calculator. FIGS. 10A-10B will be discussed in connection with FIGS. 11A-11F.

FIGS. 11A-11F together constitute an example table calculator as part of an embodiment of an Electrocardiogram (ECG) Reconsideration Risk Calculator 401. This table provides "behind the scenes" determination of a best possible rate class for each of a number of characteristics that may apply to an applicant seeking life insurance coverage. The table is merely one possible implementation of a reconsideration risk calculator.

Referring now to FIGS. 10A-10B, the Electrocardiogram (ECG) Reconsideration Risk Calculator 401 allows life insurance underwriters and sales case analysts a "self-service tool" to process the risk associated with a variety of ECG impairments by entering several additional cardiovascular tests 402, which, if submitted, may allow improvement in risk classification. The calculator 401 then determines the best risk classification 405 based on additional information without the need of sending the application to the medical director.

In FIGS. 10A-10B, along the left-hand side are shown a plurality of potential characteristics 402 that may or may not be abnormal for an applicant's ECG. The next column 403 shows a corresponding Medical Information Bureau (MIB) code for each characteristic 402. An underwriter may readily translate a MIB received in a communication from the medical director into the corresponding characteristic in 402, using a corresponding pull-down menu, if the underwriter doesn't know the MIB. The third column 404 depicts what is needed for a reconsideration to be given. The fourth column 405 displays to the underwriter the best potential rate class they could offer the applicant if a "normal" test result were produced by the designated test(s) 404 needed for reconsideration.

For example, still with reference to FIG. 10A, and considering characteristic #1, Mechanical Pacemaker, if the applicant was under 40 and could provide "normal" test results for an Echocardiogram (ECHO) and an Exercise Treadmill Test (ETT), his or her best potential rate class would be "Table B". Thus, if an applicant has an artificial pacemaker, then what's needed for reconsideration of the applicant's rate class depends upon the applicant's age group and whether "normal" results can be obtained for ECHO and ETT tests. If the applicant, for example, is age 50 and can produce normal test results for both ECHO and ETT, then the applicant's rate class would be PREF.

As a brief aside, life insurance underwriters may assign risk classes to applicants in any suitable way. One way is to assign various "tables", each representing a different degree of mortality. For example, "Table A" may represent an increase of 25% mortality (probability of death relative to average statistical death rates); "Table B" may represent 50% increased mortality; "Table C" may represent 75% increased mortality; and "Table D" may represent 100% increased mortality. In FIGS. 11A-11B, the expression "1 Table Reduced" means the assigned risk is the next lower table, e.g. Table B instead of Table C. The expression "2 Tables Reduced' means the assigned risk is two tables lower, e.g. Table B instead of Table D. The expression "PREF" may represent an average mortality. The expression "PUL", as used by some underwriters, may represent Preferred Ultra Level, the best assigned risk level.

Returning to FIG. 10A, "Dysrhythmias" means an irregular heartbeat of some sort. "Premature contractions" is a particular kind of irregular heartbeat, and the subcategories under this heading are dependent upon the number and frequency of them and the types. For example, using the pull-down menu of the user interface depicted in FIG. 10A, the underwriter may select the particular "Premature Contractions" characteristic 402 for a given applicant, and the resulting tests 404 needed for reconsideration and the best potential rate class 405 are displayed, as calculated by the table calculator shown in FIG. 11A under the heading "Premature Contractions". If the applicant had between 3 and 8 premature atrial contractions (PACs) during an ECG, then nothing further would be required for reconsideration, and the applicant would get PUL risk level. However, if the applicant had between 3 and 20 premature ventricular contractions (PVCs) during an ECG, then normal results with either ECHO or ETT would provide "1 Table Reduced", and normal results from both ECHO and ETT would provide "PUL".

Other major types of characteristics depicted in FIGS. 10A-10B (and in the corresponding table calculator of FIGS. 11A-11F) may include Rate, Atrial Fibrillation And/Or Flutter, Atrio-Ventricular (AV) Block, Wolf-Parkinson-White Syndrome (WPW), Q-Waves Abnormal, Voltage Abnormal, Axis Deviation Abnormal, ST Segment Depression And/Or T-Waves Abnormal, Bundle Branch Block, and Complex Cardiac Tests. The latter may include, as illustrated in FIG. 11F, for example, Exercise Treadmill Test (ETT), Nuclear Imaged Scan (Cardiolyte ETT or Thallium ETT), and Echo ETT, and Echocardiogram, a Holter monitor test, and/or an Electron Beam CAT Scan (EBCT) of the heart. The list of characteristics may comprise more, fewer, and/or different ones than those depicted in FIGS. 10A-10B and 11A-11B.

The table calculator shown in FIGS. 11A-11F provides one possible set of rules about what different tests are required for reconsideration of rate class for a large list of possible medical characteristics that a potential applicant could have. These rules may be determined, for example, by a medical director, based upon his or her experience, knowledge, research, and other factors. The rules represent a knowledge base of the medical director or other source of medical underwriting knowledge, such as an underwriting manual.

The ECG Reconsideration Risk Calculator 401 automates a process for re-determining risk of life insurance applicants by quickly identifying additional tests that are needed, and identifying the corresponding best potential rate class that could be offered if the test results are "normal".

If the applicant proceeds to get the additional test(s) and furnishes proof of "normal" results to the underwriter, then the underwriter can offer the applicant life insurance at the corresponding rate class.

The ECG Reconsideration Risk Calculator 401 reduces the demand on the time of life insurance companies' medical directors and improves processing time. It also provides customers with consistent information and guidance to allow them to submit additional information that may improve their rate classification. It also may reduce declination by customers of initially rated policies. An as example, these risk classifications may be calculated based on the particular information provided (e.g., ECG impairments and several additional cardiovascular tests 403) according to the table calculator shown in FIGS. 11A-11F.

The underwriter may select a "Reset All Controls" icon or device 450 to reset all of the information in FIGS. 10A-10B, and the underwriter may select a "Back to Main" icon or device 460 to return to the main screen (FIG. 9) of the Life Insurance Underwriting Risk Calculator 300.

Figure 12:
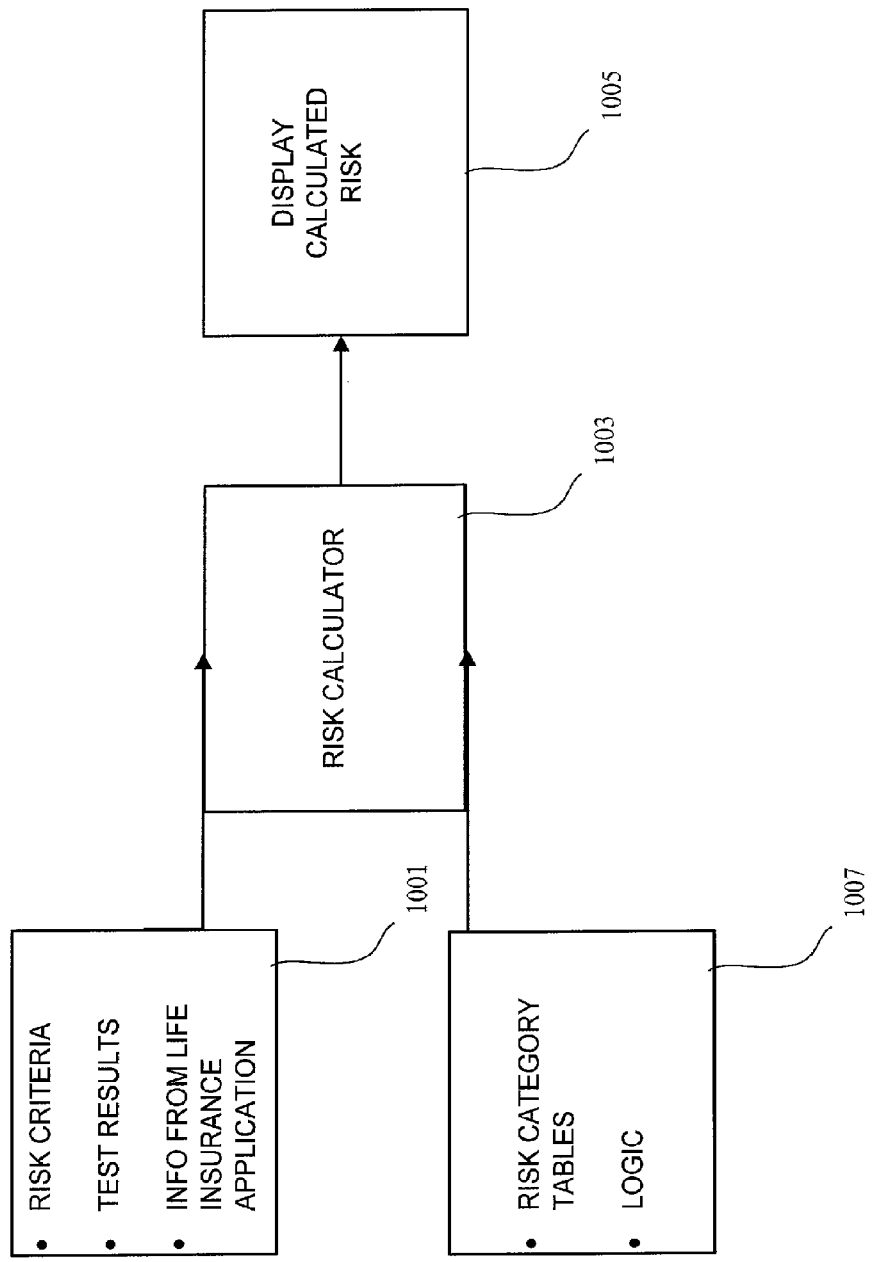
FIG. 12 is a flow diagram illustrating a process of an example life insurance underwriting risk calculator.

FIG. 12 is a flow diagram illustrating a process of an example Life Insurance Underwriting Risk Calculator. The risk criteria, test results, and information from life insurance application 1001 are entered into the risk calculator 1003. The risk calculator 1003 then references the risk category tables 1007 that have which risk category to assign based upon the values and combinations of the risk criteria 1001 entered. The calculator 1001 then outputs and displays the assigned risk category 1005 based upon the values and combinations of the risk criteria 1001 entered.

The various systems, methods, and techniques described herein may be implemented with hardware or software or, where appropriate, with a combination of both. Thus, the methods and apparatus of the present inventive subject matter, or certain aspects or portions thereof, may take the form of program code (i.e., instructions) embodied in tangible media, such as floppy diskettes, CD-ROMs, hard drives, or any other machine-readable storage medium, wherein, when the program code is loaded into and executed by a machine, such as a computer, the machine becomes an apparatus for practicing the inventive subject matter. In the case of program code execution on programmable computers, the computer will generally include a processor, a storage medium readable by the processor (including volatile and non-volatile memory and/or storage elements), at least one input device, and at least one output device. One or more programs are preferably implemented in a high level procedural or object oriented programming language to communicate with a computer system. However, the program(s) can be implemented in assembly or machine language, if desired. In any case, the language may be a compiled or interpreted language, and combined with hardware implementations.

The methods and apparatus of the present inventive subject matter may also be embodied in the form of program code that is transmitted over some transmission medium, such as over electrical wiring or cabling, through fiber optics, or via any other form of transmission, wherein, when the program code is received and loaded into and executed by a machine, such as an EPROM, a gate array, a programmable logic device (PLD), a client computer, a video recorder or the like, the machine becomes an apparatus for practicing the inventive subject matter. When implemented on a general-purpose processor, the program code combines with the processor to provide a unique apparatus that operates to perform the functionality of the systems and methods described herein.

While the present inventive subject matter has been described in connection with the preferred embodiments of the various figures, it is to be understood that other similar embodiments may be used, or modifications and additions may be made to the described embodiment for performing the same function of the present inventive subject matter without deviating there from. Furthermore, it should be emphasized that a variety of computer platforms, including handheld device operating systems and other application-specific hardware/software interface systems, are herein contemplated, especially as the number of wireless networked devices continues to proliferate. Therefore, the present inventive subject matter should not be limited to any single embodiment, but rather it should be construed in breadth and scope in accordance with the appended claims.

Finally, the disclosed embodiments described herein may be adapted for use in other processor architectures, computer-based systems, or system virtualizations, and such embodiments are expressly anticipated by the disclosures made herein and, thus, the present inventive subject matter should not be limited to specific embodiments described herein but instead construed most broadly.

Figure 13:
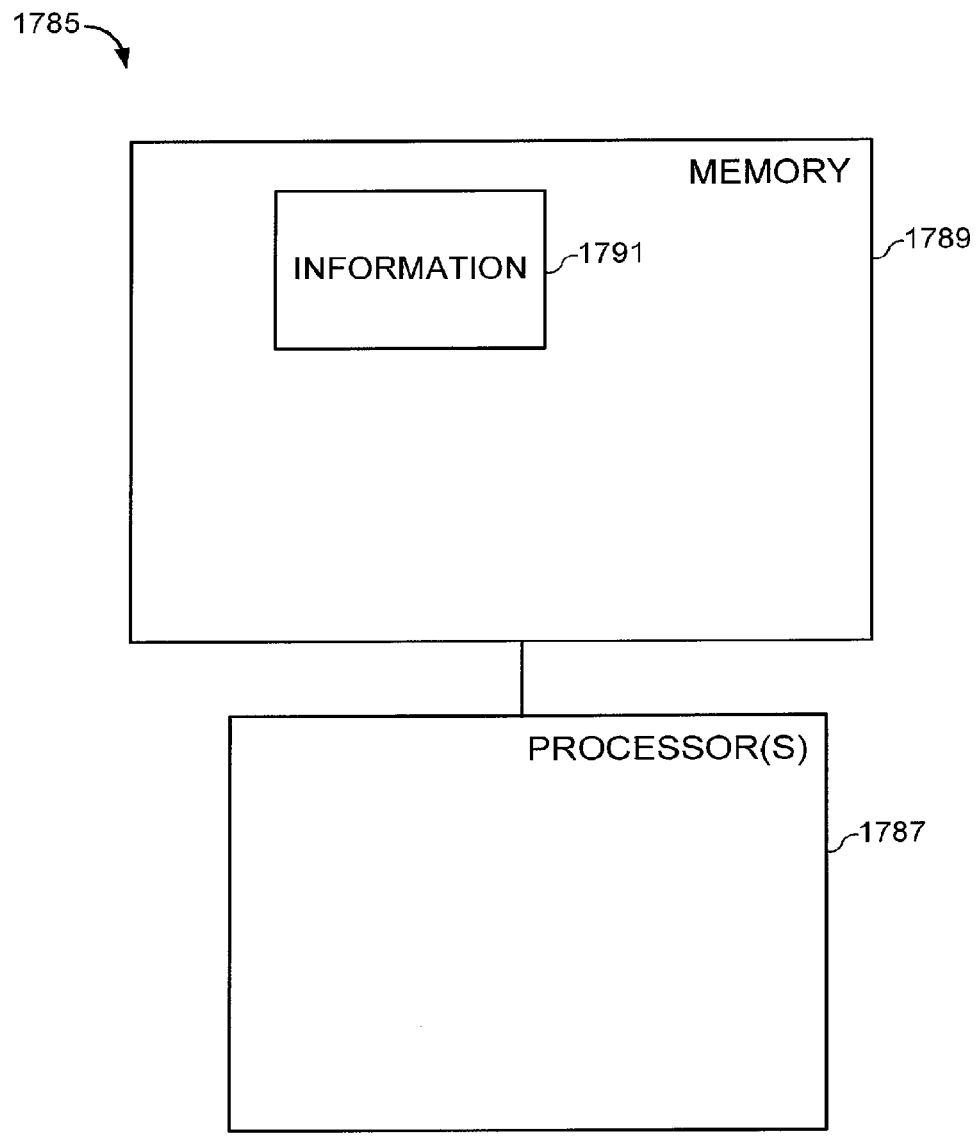
FIG. 13 is a block diagram of an article according to various embodiments.

FIG. 13 is a block diagram of an article 1785 according to various embodiments. Such embodiments may comprise a computer, a memory system, a magnetic or optical disk, some other storage device, or any type of electronic device or system. The article 1785 may include one or more processor(s) 1787 coupled to a machine-accessible medium such as a memory 1789 (e.g., a memory including electrical, optical, or electromagnetic elements). The medium may contain associated information 1791 (e.g., computer program instructions, data, or both), which, when accessed, results in a machine (e.g., the processor(s) 1787) performing the activities previously described herein.

Implementing the apparatus, systems, and methods disclosed herein may enable an underwriter to independently and accurately interpret an electrocardiogram and/or other diagnostic evidence, to derive a diagnosis and a MIB code, and to assign a correct risk class to an application for insurance. In some embodiments, the apparatus, systems, and methods disclosed herein may enable an underwriter to independently determine whether an applicant could be granted a more preferential risk class, and if so, what further action(s) the applicant would have to satisfy to reach that risk class. Improved efficiency, decreased file transfers, decreased processing delays, increased consistency among underwriters, and increased customer satisfaction may result.

The accompanying drawings that form a part hereof show, by way of illustration and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted to require more features than are expressly recited in each claim. Rather, inventive subject matter may be found in less than all features of a single disclosed embodiment. Thus the claims are hereby incorporated into the Detailed Description, with each claim standing on its own as a separate embodiment.

The invention claimed is:

1. A cardiac risk reconsideration processor-implemented method, comprising:
   obtaining an insurance application and an electrocardiogram for an applicant;
   extracting applicant cardiovascular characteristics based on the insurance application and the electrocardiogram;
   determining via a processor an initial cardiac risk classification for the applicant based on the applicant cardiovascular characteristics;
   identifying a cardiovascular test for the applicant to undergo to improve on the initial cardiac risk classification as well as a best potential cardiac risk classification, based on the extracted applicant cardiovascular characteristics; and
   providing a notification of the cardiovascular test and the best potential cardiac risk classification for the applicant.

2. The method of claim 1, further comprising:
   obtaining a test result for the identified cardiovascular test for the applicant;
   determining that the initial cardiac risk classification should be modified to the best potential cardiac risk classification based on the test result;
   generating an insurance policy for the applicant based on the best potential cardiac risk classification; and
   providing the generated insurance policy for the applicant.

3. The method of claim 1, further comprising:
   obtaining a test result for the identified cardiovascular test for the applicant; and
   determining that the initial cardiac risk classification should not be modified to the best potential cardiac risk classification based on the test result.

4. The method of claim 3, further comprising:
   generating an insurance policy for the applicant based on the initial cardiac risk classification; and
   providing the generated insurance policy for the applicant.

5. The method of claim 3, further comprising:
   identifying, upon determining that the initial cardiac risk classification should not be modified to the best potential cardiac risk classification, another cardiovascular test for the applicant to undergo to improve on the initial cardiac risk classification, based on the obtained test result; and
   providing a notification of the another cardiovascular test for the applicant.

6. The method of claim 1, wherein the identified cardiovascular test is one of: an echocardiogram; nuclear imaged scan; exercise treadmill; echo exercise treadmill; Holter monitor; and electron beam CAT scan tests.

7. The method of claim 1, wherein the applicant cardiovascular characteristics includes at least one of: premature contraction; rate; atrial fibrillation; atrio-ventricular; WPW syndrome; Q-wave; voltage; axis deviation; ST segment depression; and bundle branch characteristics.

8. A cardiac risk reconsideration system, comprising:
   a processor; and
   a memory disposed in communication with the processor and storing processor-executable instructions to:
      obtain an insurance application and an electrocardiogram for an applicant;
      extract applicant cardiovascular characteristics based on the insurance application and the electrocardiogram;
      determine an initial cardiac risk classification for the applicant based on the applicant cardiovascular characteristics;
      identify a cardiovascular test for the applicant to undergo to improve on the initial cardiac risk classification as well as a best potential cardiac risk classification, based on the extracted applicant cardiovascular characteristics; and
      provide a notification of the cardiovascular test and the best potential cardiac risk classification for the applicant.

9. The system of claim 8, the memory further storing instructions to:
   obtaining a test result for the identified cardiovascular test for the applicant;
   determining that the initial cardiac risk classification should be modified to the best potential cardiac risk classification based on the test result;
   generating an insurance policy for the applicant based on the best potential cardiac risk classification; and
   providing the generated insurance policy for the applicant.

10. The system of claim 8, the memory further storing instructions to:
    obtaining a test result for the identified cardiovascular test for the applicant; and
    determining that the initial cardiac risk classification should not be modified to the best potential cardiac risk classification based on the test result.

11. The system of claim 10, the memory further storing instructions to:
    generating an insurance policy for the applicant based on the initial cardiac risk classification; and
    providing the generated insurance policy for the applicant.

12. The system of claim 10, the memory further storing instructions to:
    identifying, upon determining that the initial cardiac risk classification should not be modified to the best potential cardiac risk classification, another cardiovascular test for the applicant to undergo to improve on the initial cardiac risk classification, based on the obtained test result; and
    providing a notification of the another cardiovascular test for the applicant.

13. The system of claim 8, wherein the identified cardiovascular test is one of: an echocardiogram; nuclear imaged scan; exercise treadmill; echo exercise treadmill; Holter monitor; and electron beam CAT scan tests.

14. The system of claim 8, wherein the applicant cardiovascular characteristics includes at least one of: premature contraction; rate; atrial fibrillation; atrio-ventricular; WPW syndrome; Q-wave; voltage; axis deviation; ST segment depression; and bundle branch characteristics.

15. A processor-readable tangible medium storing processor-executable cardiac risk reconsideration instructions to:
    obtain an insurance application and an electrocardiogram for an applicant;
    extract applicant cardiovascular characteristics based on the insurance application and the electrocardiogram;
    determine an initial cardiac risk classification for the applicant based on the applicant cardiovascular characteristics;
    identify a cardiovascular test for the applicant to undergo to improve on the initial cardiac risk classification as well as a best potential cardiac risk classification, based on the extracted applicant cardiovascular characteristics; and provide a notification of the cardiovascular test and the best potential cardiac risk classification for the applicant.

16. The medium of claim 15, further storing instructions to:
obtaining a test result for the identified cardiovascular test for the applicant;
determining that the initial cardiac risk classification should be modified to the best potential cardiac risk classification based on the test result;
generating an insurance policy for the applicant based on the best potential cardiac risk classification; and
providing the generated insurance policy for the applicant.

17. The medium of claim 15, further storing instructions to:
obtaining a test result for the identified cardiovascular test for the applicant; and
determining that the initial cardiac risk classification should not be modified to the best potential cardiac risk classification based on the test result.

18. The medium of claim 17, further storing instructions to:
generating an insurance policy for the applicant based on the initial cardiac risk classification; and
providing the generated insurance policy for the applicant.

19. The medium of claim 17, further storing instructions to:
identifying, upon determining that the initial cardiac risk classification should not be modified to the best potential cardiac risk classification, another cardiovascular test for the applicant to undergo to improve on the initial cardiac risk classification, based on the obtained test result; and
providing a notification of the another cardiovascular test for the applicant.

20. The medium of claim 15, wherein the identified cardiovascular test is one of: an echocardiogram; nuclear imaged scan; exercise treadmill; echo exercise treadmill; Holter monitor; and electron beam CAT scan tests.

21. The medium of claim 15, wherein the applicant cardiovascular characteristics includes at least one of: premature contraction; rate; atrial fibrillation; atrio-ventricular; WPW syndrome; Q-wave; voltage; axis deviation; ST segment depression; and bundle branch characteristics.

* * * * *